United States Patent
Belanger et al.

(10) Patent No.: US 11,511,213 B2
(45) Date of Patent: Nov. 29, 2022

(54) NICKEL-COBALT ALLOY MATERIAL DEVICES AND COMPONENTS

(71) Applicant: Waters Technologies Corporation, Milford, MA (US)

(72) Inventors: Jonathan L. Belanger, Whitinsville, MA (US); Hua Yang, Franklin, MA (US); Edouard S. P. Bouvier, Stow, MA (US); Mathew DeLano, Allston, MA (US); Raymond P. Fisk, Norton, MA (US); Hillary B. Hewitson, Sharon, MA (US); Wade P. Leveille, Douglas, MA (US); Kevin Daniel Wyndham, Upton, MA (US)

(73) Assignee: Waters Technologies Corporation, Milford, MA (US)

(*) Notice: Subject to any disclaimer, the term of this patent is extended or adjusted under 35 U.S.C. 154(b) by 817 days.

(21) Appl. No.: 15/752,121

(22) PCT Filed: Aug. 12, 2016

(86) PCT No.: PCT/US2016/046752
§ 371 (c)(1),
(2) Date: Feb. 12, 2018

(87) PCT Pub. No.: WO2017/027796
PCT Pub. Date: Feb. 16, 2017

(65) Prior Publication Data
US 2018/0236379 A1    Aug. 23, 2018

Related U.S. Application Data

(60) Provisional application No. 62/204,769, filed on Aug. 13, 2015.

(51) Int. Cl.
*B01D 15/22* (2006.01)
*G01N 30/60* (2006.01)
(Continued)

(52) U.S. Cl.
CPC ............ *B01D 15/22* (2013.01); *B01D 53/02* (2013.01); *B01D 53/025* (2013.01);
(Continued)

(58) Field of Classification Search
None
See application file for complete search history.

(56) References Cited

U.S. PATENT DOCUMENTS

| 3,878,092 A | 4/1975 | Fuller |
| 7,896,935 B2 | 3/2011 | Tonkovich et al. |

(Continued)

FOREIGN PATENT DOCUMENTS

| EP | 1795264 B1 | 8/2012 |
| EP | 0978311 B1 | 11/2014 |

(Continued)

OTHER PUBLICATIONS

International Search Report and Written Opinion for International Application No. PCT/US2016/046752, competed on Nov. 30, 2016 and dated Dec. 28, 2016 (18 Pages).

*Primary Examiner* — Kara M Peo
(74) *Attorney, Agent, or Firm* — Womble Bond Dickinson (US) LLP; Deborah M. Vernon

(57) ABSTRACT

Exemplary embodiments are directed to devices for separating a sample by chromatography, components of the devices, and methods for using the devices, and directed to devices and components for use with immobilized enzymatic reactors. A device includes a wall having a wetted surface exposed to a mobile phase including the sample during chromatographic separation. The wetted surface of the wall includes an alloy material including the following constituents: nickel, and cobalt and/or chromium where the alloy is limited in an amount of titanium to 1 wt %. A component includes a body having a wetted surface exposed (Continued)

to a mobile phase including the sample during chromatographic separation. The wetted surface of the body includes an alloy material including the following constituents: nickel, and cobalt and/or chromium where the alloy is limited in an amount of titanium to 1 wt %.

20 Claims, 20 Drawing Sheets

(51) Int. Cl.
*B01D 53/02* (2006.01)
*C12M 1/40* (2006.01)
*C12M 1/00* (2006.01)
*B01L 3/00* (2006.01)
*G01N 30/72* (2006.01)
*G01N 30/88* (2006.01)

(52) U.S. Cl.
CPC ............ *C12M 21/18* (2013.01); *C12M 23/20* (2013.01); *G01N 30/6052* (2013.01); *G01N 30/6073* (2013.01); *G01N 30/6095* (2013.01); *B01D 2253/1122* (2013.01); *B01L 3/502753* (2013.01); *G01N 30/7266* (2013.01); *G01N 2030/8831* (2013.01)

(56) References Cited

U.S. PATENT DOCUMENTS

| 8,785,843 | B2 | 7/2014 | Jones et al. |
| 2009/0069697 | A1 | 3/2009 | Frazier et al. |
| 2009/0130735 | A1 | 5/2009 | Simon et al. |
| 2010/0065141 | A1 | 3/2010 | Plant |
| 2010/0105570 | A1 | 4/2010 | Studer et al. |
| 2012/0118735 | A1 | 5/2012 | Kim et al. |
| 2012/0132794 | A1 | 5/2012 | Buchanan et al. |
| 2013/0014567 | A1 | 1/2013 | Bunner et al. |
| 2013/0193052 | A1 | 8/2013 | Witt et al. |
| 2014/0271774 | A1 | 9/2014 | Drumheller et al. |

FOREIGN PATENT DOCUMENTS

| WO | 2002/018929 A2 | 3/2002 |
| WO | 2014/201033 A1 | 12/2014 |

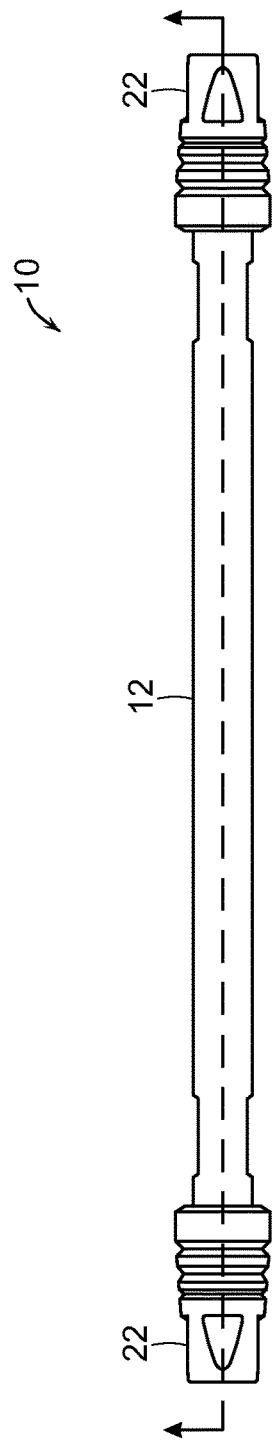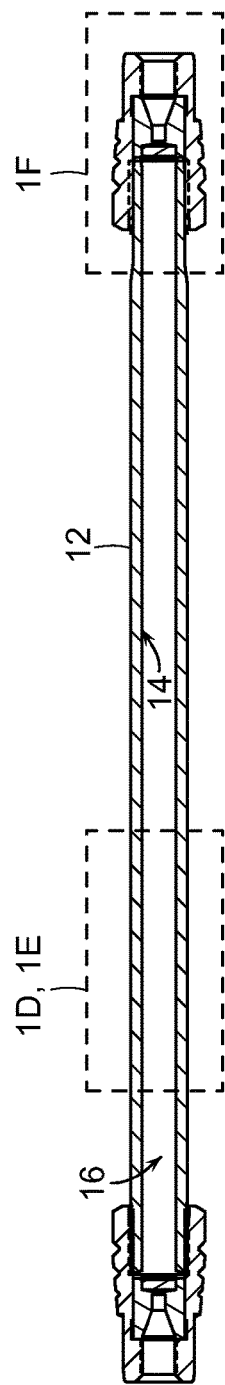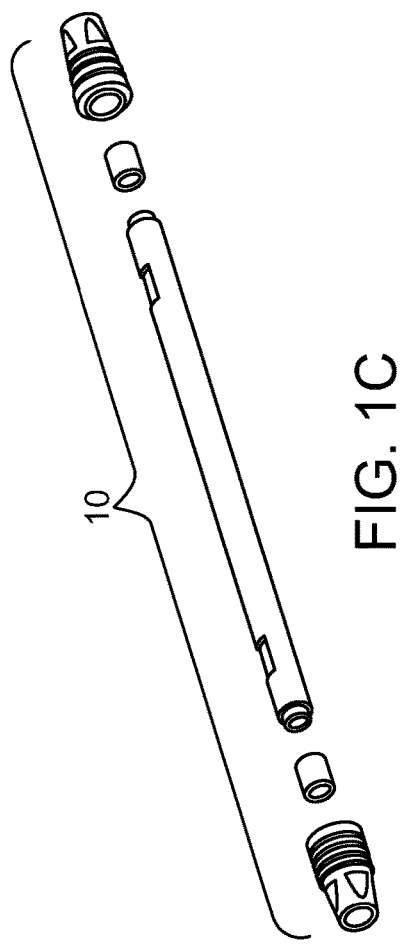
FIG. 1A
FIG. 1B
FIG. 1C

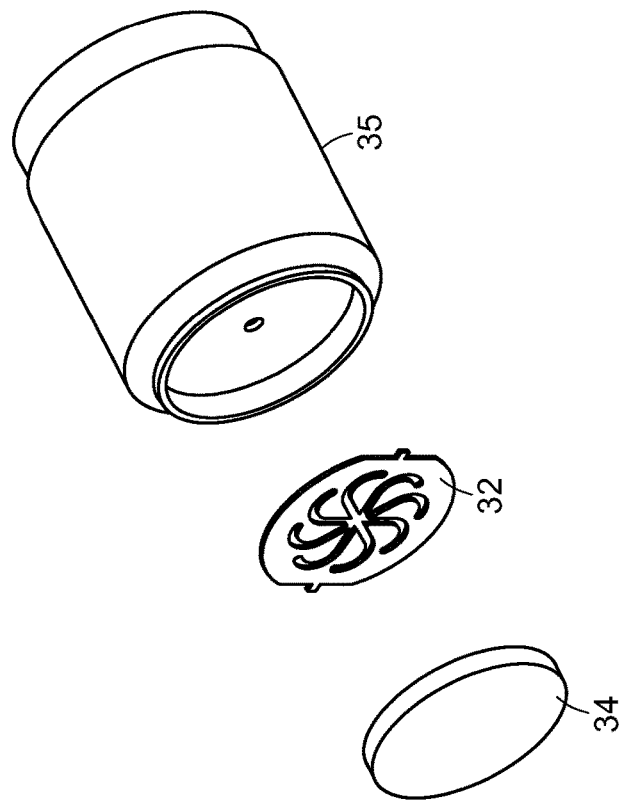
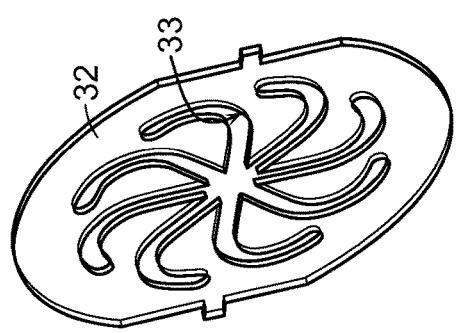
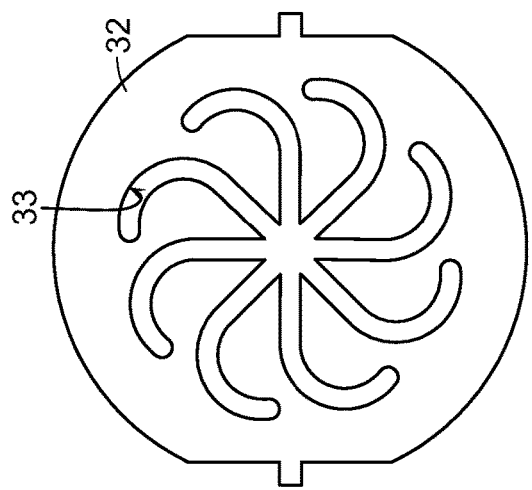

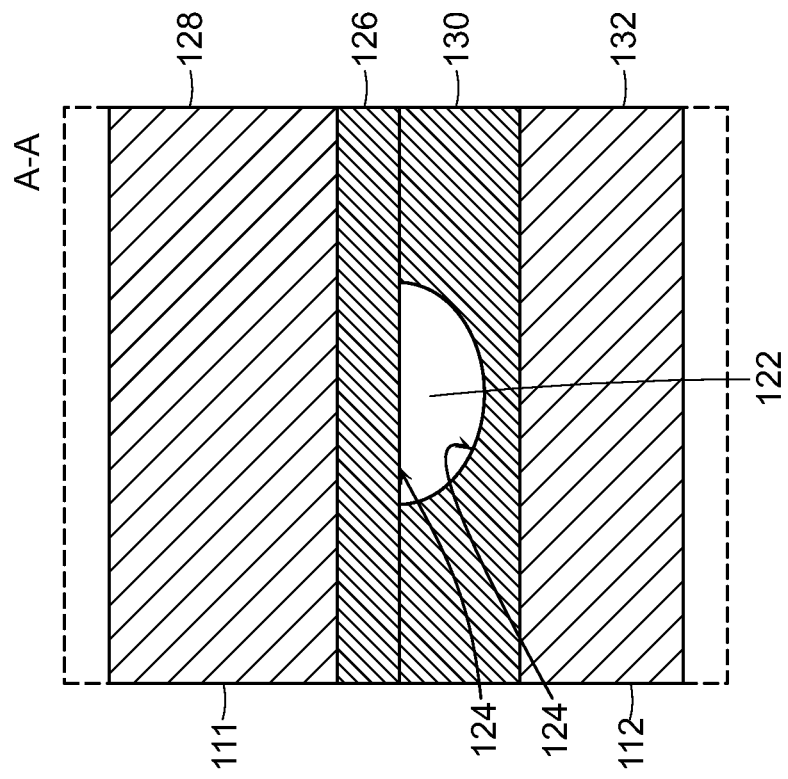
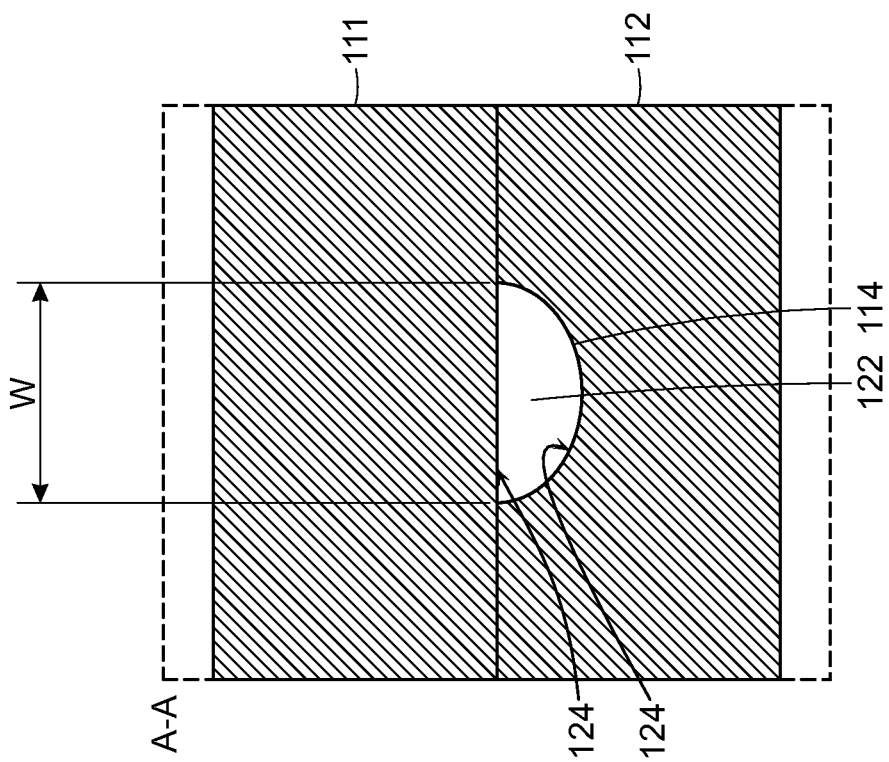
FIG. 6B
FIG. 6C

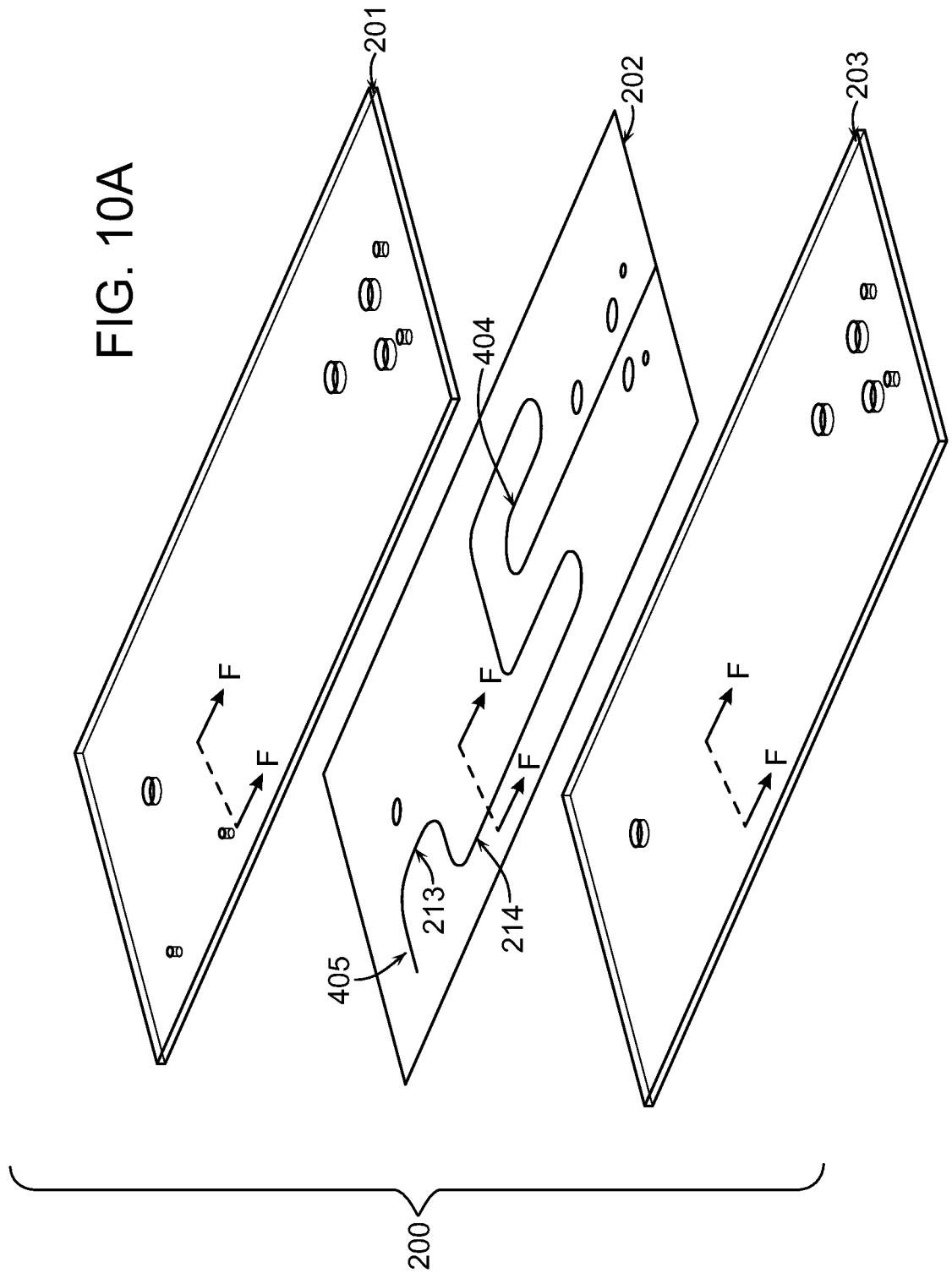

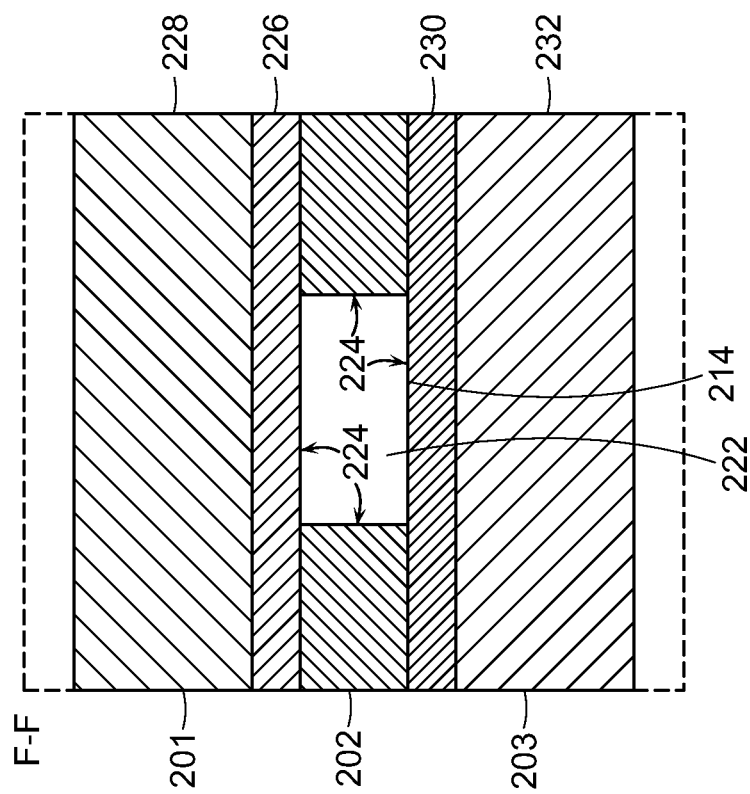
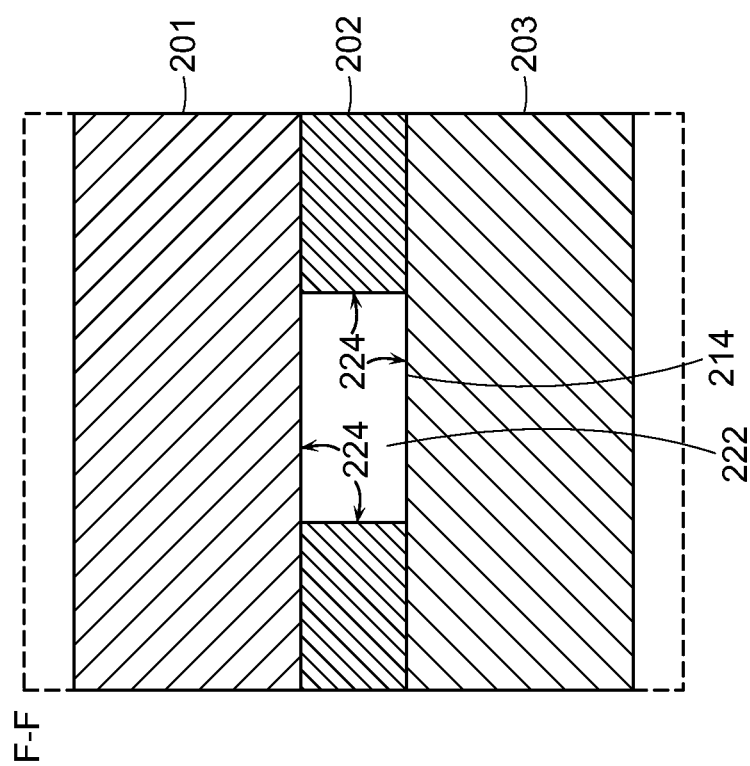
FIG. 10C
FIG. 10B

FIG. 13    Stainless Steel Column
Peak width @ 5% peak height
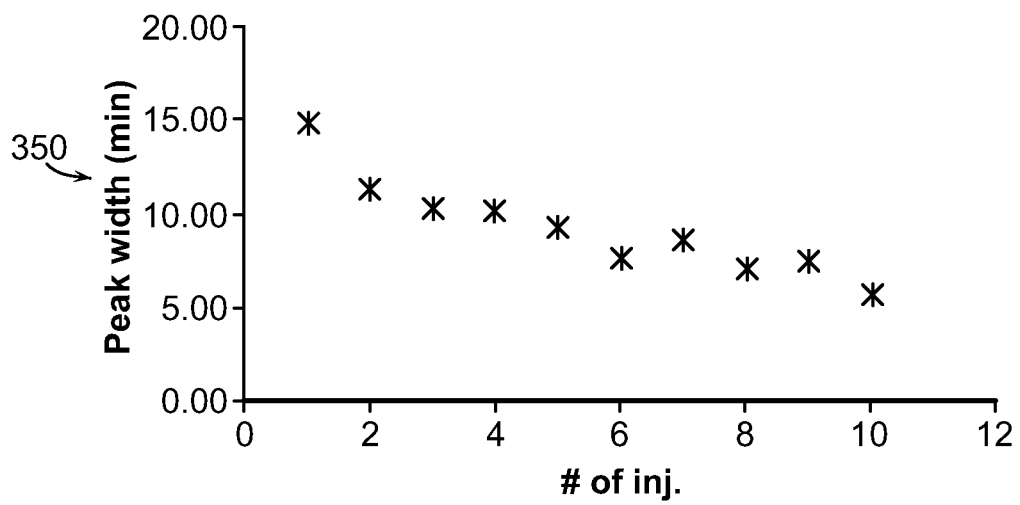
FIG. 14    Fused Silica Column
Peak width @ 5% peak height
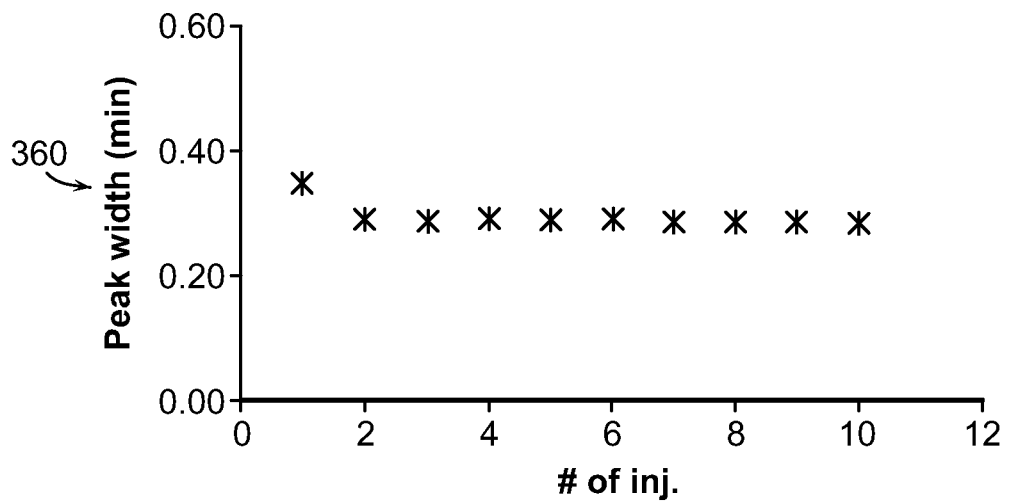

NICKEL-COBALT ALLOY MATERIAL DEVICES AND COMPONENTS

CROSS-REFERENCE TO RELATED APPLICATION

This application is a National Stage Application of international application no. PCT/US2016/046752, entitled "Nickel-Cobalt Alloy Material Devices and Components," which claims priority to and benefit of U.S. Provisional Patent Application No. 62/204,769, entitled "Nickel-Cobalt Alloy Material as Column Hardware for Chromatographic Separation of Biological Samples," filed Aug. 13, 2015, which is incorporated by referenced herein in its entirety.

TECHNICAL FIELD

This disclosure relates to materials for chromatographic separation devices and components and materials for immobilized enzymatic reactor devices and components.

BACKGROUND

Chromatographic techniques are important tools for the identification and separation of complex samples. The basic principle underlying chromatographic techniques is the separation of a mixture into individual components by transporting the mixture in a moving fluid through a retentive media in a separation channel (e.g., a separation column). The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation. A detector, positioned at the outlet end of the separation channel, detects each of the separated components as they exit the separation channel yielding a chromatogram.

The methods of choice for chromatographic separations have conventionally been gas chromatography (GC) and liquid chromatography (LC). One major difference between GC and LC is that the mobile phase in GC is a gas, whereas the mobile phase in LC is a liquid. Although GC is typically a sensitive method of analysis, the high temperatures required in GC make this method unsuitable for some high molecular weight biopolymers or proteins because they are denatured by heat. In addition, their low vapor pressure makes them insoluble in the gas phase. In contrast, LC does not require high temperatures and can utilize solubilizing mobile phases. LC that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure, which is the mobile phase, through a separation channel (e.g., a column) that is packed with a stationary phase, which is typically composed of irregularly or spherically shaped particles. In some embodiments, the stationary phase may be a monolithic solid.

Various materials (e.g., stainless steel, polymers such as PEEK, fused silica, etc.) have been used for column hardware (e.g., HPLC hardware or UPLC hardware) for chromatographic separation. However, each of these categories of materials exhibits deficiencies with respect to chromatographic separation of peptides and proteins in biological samples.

SUMMARY

Some exemplary embodiments of the present technology include devices for separating a sample by chromatography and components for chromatographic separation devices. The devices or components have a wetted surface exposed to a mobile phase including the sample during chromatographic separation. The wetted surface includes an alloy material comprising nickel, cobalt and chromium and limited in an amount of titanium. In some embodiments, the alloy material of the wetted surface enables chromatography of samples containing peptides (e.g., histidine-containing peptides) with narrow peaks for the peptide components and without significant peak tailing of the peptide components. In some embodiments, the alloy material is more corrosion-resistant that other materials, such as stainless steel, employed in some chromatographic separation devices. The enhanced corrosion resistance of alloys employed may increase a useful lifetime of chromatographic separation devices and components.

In some aspects, components and devices for separating a sample by chromatography have wetted surfaces exposed to a mobile phase including the sample with one or more of the wetted surfaces including an alloy material selected to resist adsorption of proteins and peptides present in the sample. In an embodiment, the alloy material is a nickel-cobalt, nickel-cobalt-chromium, or nickel-chromium alloy material and is limited in an amount of titanium (e.g., less than 1 wt % titanium, less than 0.5 wt % titanium, less than 0.1 wt % titanium, less than 0.05 wt % titanium, less than 0.015 wt % titanium, less than 0.01 wt % titanium, less than 0.005 wt % titanium, less than 0.001 wt % titanium). In an embodiment, the alloy material has a composition of about 35 wt % cobalt, 35 wt % nickel, 20 wt % chromium, and 10 wt % molybdenum and is limited in an amount of titanium. In some aspects, the alloy material is included in a surface portion of a chromatography component or separation channel with a bulk portion of the chromatography component or separation channel includes a different material. In an example, the surface portion and the bulk portion are diffusion bonded to each other.

In some aspects, the components and devices having wetted surfaces including the alloy material are configured for use in microfluidic separation devices or systems (e.g., where a width or diameter of a separation channel falls in a range of 20 μm to 500 μm). In some aspects, the components and devices having wetted surfaces including the alloy material are configured for use at high pressures (e.g., at pressures in a range of 6,000 to 15,000 psi).

In one aspect, a device for separating a sample by chromatography includes a wall having a wetted surface exposed to a mobile phase including the sample during chromatographic separation. The wetted surface of the wall includes an alloy material including the following constituents: nickel; and cobalt and/or chromium; and limited in an amount of titanium to 1 wt %. In some embodiments, the wetted surface of the wall comprises the alloy material.

In some embodiments, the wall includes a surface portion including the wetted surface and a bulk portion, and the composition of the alloy material of the wetted surface is different than a composition of a material of the bulk portion. In some embodiments, the surface portion is diffusion bonded to the bulk portion. In some embodiments, most or all of the thickness of the wall may be made of the alloy.

In some embodiments, the wetted surface of the wall defines a separation channel. In some embodiments, the device further includes an electrospray tip at an outlet of the separation channel and a wetted surface of the electrospray tip includes the alloy material.

In some embodiments, the device includes two or more sheets of the alloy material, a portion of each sheet forming a portion of the wall. In some embodiments, the two or more sheets are diffusion bonded at an interface with at least a portion of the separation channel extending along the interface.

In some embodiments, the device includes two or more sheets, each sheet including a layer of the alloy material and each sheet forming a portion of the wall with the layer of alloy material of the sheet forming the wetted surface for the portion of the wall. In some embodiments, the layers of the alloy material of the two or more sheets are diffusion bonded at an interface with at least a portion of the separation channel extending along the interface.

In some embodiments, the device also includes an end fitting and wetted surfaces of the end fitting include the alloy material.

In some embodiments, the device also includes a seal ring and wetted surfaces of the seal ring include the alloy material. In some embodiments, the seal ring includes a frit and wetted surfaces of the frit include the alloy material.

In some embodiments, the device also includes a frit and wetted surfaces of the frit comprise the alloy material.

In some embodiments, the device also includes a weir and wetted surfaces of the weir comprise the alloy material.

In some embodiments, the device also includes one or more integrated valves, and wetted surfaces of the one or more integrated valves comprise the alloy material.

In some embodiments, the device also includes a distributor disk and wetted surfaces of the distributor disk include the alloy material.

In some embodiments, all surfaces of the device upstream of an outlet end of the separation channel and configured to be in contact with the mobile phase including the sample during use, excluding the stationary phase, include the alloy material.

In some embodiments, the width or diameter of the separation channel falls in a range of 500 μm to 50 mm.

In some embodiments, the device is a microfluidic device and the width or diameter of the separation channel falls in a range of 20 μm to 500 μm.

In some embodiments, the width or diameter of the separation channel falls in a range of 500 μm to 50 mm.

In another aspect, a component configured for use in a device for separating a sample by chromatography includes a body having a wetted surface exposed to a mobile phase including the sample during chromatographic separation. The wetted surface includes an alloy material including the following constituents: nickel; and cobalt and/or chromium; and limited in an amount of titanium to 1 wt %.

In some embodiments, the wetted surface defines a separation channel through which the mobile phase including the sample flows during use. In some embodiments, a width or diameter of the separation channel is between 20 μm and 500 μm. In some embodiments, the component further includes an electro spray tip at an outlet of the separation channel, and the wetted surface of the body includes a wetted surface of the electro spray tip.

In some embodiments, the component further includes one or more integrated valves, and wetted surfaces of the one or more integrated valves include the alloy material.

In some embodiments, the component is an end fitting for an inlet or an outlet of a separation column.

In some embodiments, the component is a stationary phase retaining element configured to keep a stationary phrase within a separation channel of the device. In some embodiments, the stationary phase retaining element is a frit. In some embodiments, the stationary phase retaining element is a weir structure.

In some embodiments, the body includes a surface portion including the wetted surface and a bulk portion, and a composition of the alloy material of the wetted surface is the same as a composition of a material of the bulk portion. In some embodiments, the body includes a surface portion including the wetted surface and a bulk portion, and a composition of the alloy material of wetted surface is different than a composition of a material of the body portion. In some embodiments, the surface portion is diffusion bonded to the bulk portion.

In some embodiments, the wetted surface consists of the alloy material.

In one aspect, a solid body configured for use as at least part of a stationary phase in a chromatographic separation device includes an alloy material as described herein.

In another aspect, a method of performing chromatographic separation on a sample includes providing a chromatographic separation device including a separation channel. The separation channel has wetted surfaces including an alloy material including the following constituents: nickel; and cobalt and/or chromium; and limited in an amount of titanium to 1 wt %. The method also includes flowing a mobile phase carrying the sample into and through the separation channel, thereby performing chromatographic separation on the sample.

In some embodiments, the method also includes detecting components of the sample downstream of the separation channel.

In some embodiments, the sample includes proteins and the proteins in the sample are separated and detected. In some embodiments, the sample includes peptides and the peptides in the sample are separated and detected. In some embodiments, the sample comprises histidine-containing peptides and the histidine-containing peptides in the sample are separated and detected. In some embodiments, the sample includes phosphopeptides and the phosphopeptides in the sample are separated and detected.

In some embodiments, the method also includes detecting components of the sample downstream of the separation channel where the sample includes one or more of proteins or peptides, and the one or more proteins or peptides in the sample are separated and detected with a tailing factor of less than 1.3.

In another aspect, a method of performing chromatographic separation includes providing a chromatographic separation device in accordance with any embodiments described herein and flowing a mobile phase carrying a sample through the chromatographic separation device, thereby separating components of the sample.

Some exemplary embodiments of the present technology includes devices or components for performing enzymatic reactions that may be part of immobilized enzymatic reactor (IMER) systems. The devices configured for performing enzymatic reactions include a wall defining a chamber having an inlet and an outlet with the wall having a wetted surface exposed to a liquid sample during use. The wetted surface of the wall includes any of the alloy materials described herein. The components configured for performing enzymatic reactions include a body having a having a wetted surface exposed to a liquid sample during use with the wetted surface including any of the alloys described herein.

In some embodiments, the wall or the body comprises a surface portion including the wetted surface and a bulk portion, and the composition of the alloy material of the wetted surface is different than a composition of a material of the bulk portion. In some embodiments, the surface portion is diffusion bonded to the bulk portion. In some embodiments, the surface portion consists of the alloy material.

Embodiments can include one or more of the following features.

In some embodiments, the alloy material is limited in an amount of titanium to 0.1 wt %. In some embodiments, the alloy material is limited in an amount of titanium to 0.05 wt %. In some embodiments, the alloy material is limited in an amount of titanium to 0.02 wt %. In some embodiments, the alloy material is limited in an amount of titanium to 0.015 wt %. In some embodiments, the alloy material is limited in an amount of titanium to less than 0.01 wt %. In some embodiments, the alloy material is limited in an amount of titanium to less than 0.005 wt %. In some embodiments, the alloy material is limited in an amount of titanium to less than 0.001 wt % titanium.

In some embodiments, the alloy material includes both cobalt and chromium as constituents. In some embodiments, the alloy material further includes molybdenum as a constituent.

In some embodiments, the alloy material includes the following constituents: 22 wt %-45 wt % cobalt; 25 wt %-45 wt % nickel; 10 wt %-30 wt % chromium; and 0 wt %-20 wt % molybdenum; and a remainder being limited to a total of 5 wt %. In some embodiments, the remainder is limited to a total of 3 wt %.

In some embodiments, the alloy material includes the following constituents: 30 wt %-40 wt % cobalt; 30 wt %-40 wt % nickel; 15 wt %-25 wt % chromium; and 5 wt %-15 wt % molybdenum; and a remainder being limited to a total of 5 wt %. In some embodiments, the remainder is limited to a total of 3 wt %.

In some embodiments, the alloy material includes the following constituents: 32 wt %-38 wt % cobalt; 32 wt %-38 wt % nickel; 17 wt %-23 wt % chromium; and 7 wt %-13 wt % molybdenum; and limited in an amount of titanium to 0.1 wt %; and a remainder being limited to a total of 5 wt %. In some embodiments, the remainder is limited to a total of 3 wt %.

In some embodiments, the alloy material includes the following constituents: 34 wt %-36 wt % cobalt; 34 wt %-36 wt % nickel; 19 wt %-21 wt % chromium; and 9 wt %-11 wt % molybdenum; and limited in an amount of titanium to 0.05 wt %; and a remainder being limited to a total of 5 wt %. In some embodiments, the remainder is limited to a total of 3 wt %.

In some embodiments a wetted surface consists of the alloy material. In some embodiments, most of the surface area of the wetted surface is covered by the alloy material. In some embodiments, over 90% of the surface area of the wetted surface is covered by the alloy material. In some embodiments, over 95% of the surface area of the wetted surface is covered by the alloy material. In some embodiments, over 98% of the surface area of the wetted surface is covered by the alloy material. In some embodiments, over 99% of the surface area of the wetted surface is covered by the alloy material.

In some embodiments, the device or component is configured for use in ion exchange chromatography. In some embodiments, the device or component is configured for use in reversed-phase chromatography.

In some embodiments, the device or component is configured to withstand pressures used in high performance liquid chromatography. In some embodiments, the device or component is configured to withstand pressures used in ultra-high performance liquid chromatography. In some embodiments, the device or component is configured to withstand pressures of 15,000 to 20,000 psi. In some embodiments, the device or component is configured to withstand pressures of 20,000 psi to 50,000 psi. In some embodiments, the device or component is configured for low pressure applications.

In some embodiments, the alloy material is resistant to adsorption of proteins and resistant to adsorption of peptides. In some embodiments, the alloy material is resistant to adsorption of histidine-containing peptides. In some embodiments, the alloy material is resistant to adsorption of phosphopeptides.

Other advantages and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the devices and components and associated methods, reference is made to the accompanying figures, which are not necessarily to scale.

FIG. 1A is a side view of an example column assembly, in accordance with an embodiment.

FIG. 1B is a side cross-sectional view of the example column assembly of FIG. 1A.

FIG. 1C is an exploded perspective view of the example column assembly of FIG. 1A.

FIG. 5A is a perspective view of a distributor disk in accordance with an embodiment.

FIG. 5B is a front view of the distributor disk of FIG. 5A.

FIG. 5C is an exploded perspective view of the distributor disk and an accompanying housing, in accordance with an embodiment.

FIG. 6B is a cross-sectional detail view of device of FIG. 6A taken along line A-A.

FIG. 6C is a cross-sectional detail view of the device of FIG. 6A taken along line A-A showing the two layers having surface portions and bulk portions, in accordance with an embodiment.

FIG. 10A is an exploded perspective view of a three layer planar chromatographic device in accordance with an embodiment.

FIG. 10B is a cross-sectional detail view of device of FIG. 10A taken along line F-F.

FIG. 10C is a cross-sectional view of the device of FIG. 10A taken along line F-F showing a first layer and a third layer having surface portions and bulk portions, in accordance with an embodiment.

FIG. 13 is a plot of peak width as a function of injection number during analysis of a sample of an enolase tryptic digest performed using a stainless steel column.

FIG. 14 is a plot of peak width as a function of injection number during analysis of a sample of an enolase tryptic digest performed using a fused silica column.

DETAILED DESCRIPTION OF EXEMPLARY EMBODIMENTS

Figure 1D:
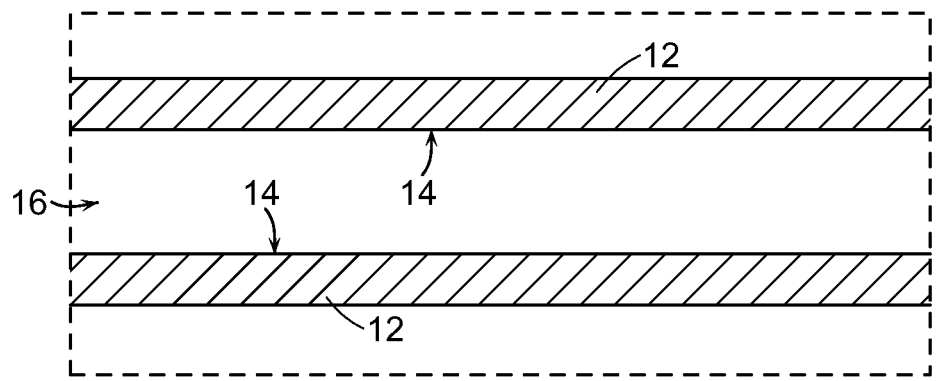
FIG. 1D is a detail view of FIG. 1B showing a portion of wall.

Stainless steel has been widely used as column hardware (e.g., HPLC hardware or UPLC hardware) for chromatographic separation. However, it has been found that some components of biological samples, such as peptides and proteins, often adsorb to column hardware of stainless steel and similar metals during analysis. It has been theorized that the adsorption is due to interaction between the peptides and the iron contained in the metal. The adsorption to column hardware during analysis causes disappearance of or reduced signal from these components in the chromatogram, or substantial peak broadening (see description accompanying FIG. 11 below).

Further, the effect of the adsorption on the chromatograph may vary for subsequent injections until the adsorption on the hardware reaches a saturation level, indicating that the column needs to be conditioned prior to analysis (see description accompanying FIG. 14 below). Stainless steel column hardware can be conditioned by injecting large quantities of peptide or protein prior to the analysis, which reduces the amount of adsorption of these components from samples during analysis. However, this may only be a temporary fix. Further, conditioning may waste sample and increases the time and effort required to obtain useful results.

Another approach to address adsorption of components of biological samples during analysis is to passivate surfaces of the hardware that will contact with the sample during analysis. It has been theorized that the adsorption is due to interaction between components, such as peptides, and the iron contained in the stainless steel or other metal used for column hardware. In one approach, stainless steel hardware may be exposed to an acid that preferentially dissolves iron, resulting in iron-deficient and chromium-rich material at the surface of the stainless steel hardware and presumably decreasing adsorption. However, this passivation may only be a temporary solution. For example, the iron-deficient surface may be damaged (e.g., scratched by the stationary phase) during use, exposing the underlying iron-rich stainless steel. Further, passivation of narrow bore tubes, such as tubes with an inner diameter of 300 μm or less, is difficult to perform reproducibly and inexpensively in a manufacturing environment.

Alternatively, non-metal materials could be employed for the surfaces of column hardware to avoid problems of adsorption of biological sample components on metal surfaces. Polymers such as polyether ether ketone (PEEK) could be used for column hardware instead of metals such as stainless steel, except that polymer materials do not have sufficient mechanical strength to be used at the high pressures required for HPLC and UHPLC. Alternatively, stainless steel columns could be sleeved or coated with polymers such as PEEK or polytetrafluoroethylene (e.g., TEFLON from DuPont). While this approach would increase the mechanical strength of the columns, it would be difficult to manufacture coated or sleeved columns with small diameters, particularly those having a diameter of less than 2 mm. Further, polymeric materials may deleteriously adsorb proteins and peptides by hydrophobic interaction when using highly aqueous mobile phases such as those employed in size-exclusion and ion-exchange chromatography. Alternatively, fused silica could be used instead of stainless steel for the column; however, it is more difficult to manufacture columns from fused silica than from stainless steel. Additionally, the silanols on the fused silica surface can interact with proteins and peptides by ion exchange.

Some embodiments described herein address or avoid problems arising from the use of conventional column materials such as stainless steel, polymers such as PEEK, and silica for chromatographic column components when performing chromatography on biological samples including peptides (e.g., histidine-containing peptides) and proteins. Embodiments include devices for separating a sample by chromatography, components configured for use in a device for separating a sample by chromatography, and methods for performing chromatographic separation on a sample. In device and component embodiments, the device or component includes a wetted surface exposed to a mobile phase including the sample during chromatographic separation with the wetted surface of the wall including an alloy material. The alloy material includes nickel, cobalt and/or chromium and is limited in an amount of titanium. In some embodiments, the alloy is resistant to adsorption of proteins and resistant to the adsorption of peptides (e.g., histidine-containing peptides).

FIGS. 1A through 1C depict a device in the form of a chromatographic column assembly 10 for separating a sample by chromatography, in accordance with an embodiment. Device 10 includes a wall 12 having a wetted surface 14 that is exposed to a mobile phase including the sample during chromatographic separation. The wetted surface 14 of the wall includes an alloy material that includes the following constituents: nickel, cobalt and/or chromium; and limited in an amount of titanium to 1 wt %. In some embodiments, the wetted surface of the wall defines a separation channel 16, as shown.

In some embodiments, the alloy material is limited in an amount of titanium to 0.1 wt %. In some embodiments, the alloy material is limited in an amount of titanium to 0.02 wt %. In some embodiments, the alloy material is limited in an amount of titanium to 0.015 wt %.

In some embodiments, the alloy includes both cobalt and chromium as constituents. In some embodiments, the alloy material further includes molybdenum as a constituent.

In some embodiments, the alloy material includes the following constituents: 25 wt %-45 wt % cobalt; 25 wt %-45 wt % nickel; 10 wt %-30 wt % chromium; and 0 wt %-20 wt % molybdenum; limited in an amount of titanium to 1 wt %; and a remainder being limited to a total of 5 wt %. In some embodiments, the reminder is limited to a total of 3 wt %

In some embodiments, the alloy material includes the following constituents: 30 wt %-40 wt % cobalt; 30 wt %-40 wt % nickel; 15 wt %-25 wt % chromium; and 5 wt %-15 wt % molybdenum; limited in an amount of titanium to 1 wt %; and a remainder being limited to a total of 5 wt %. In some embodiments, the reminder is limited to a total of 3 wt %

In some embodiments, the alloy material includes the following constituents: 32 wt %-38 wt % cobalt; 32 wt %-38 wt % nickel; 17 wt %-23 wt % chromium; and 7 wt %-13 wt % molybdenum; limited in an amount of titanium to 0.1 wt %; and a remainder being limited to a total of 5 wt %. In some embodiments, the reminder is limited to a total of 3 wt %

In some embodiments, the alloy material includes the following constituents: 34 wt %-36 wt % cobalt; 34 wt %-36 wt % nickel; 19 wt %-21 wt % chromium; and 9 wt %-11 wt % molybdenum; limited in an amount of titanium to 0.05 wt %; and a remainder being limited to a total of 5 wt %. In some embodiments, the reminder is limited to a total of 3 wt %.

For example, in some embodiments, the alloy may be MP35N LT a trademark of SPS Technologies, LLC of Jenkintown, Pa., which is comprised of approximately 35 wt % cobalt, 35 wt % nickel, 20 wt % chromium, and 10 wt % molybdenum with less than 0.01 wt % titanium. This alloy is known to have strong mechanical properties and can withstand high pressures, such as those used in UHPLC.

In some embodiments the alloy material is resistant to adsorption of proteins and resistant to adsorption of peptides. In some embodiments the alloy material is resistant to adsorption of histidine-containing peptides. In some embodiments, the alloy material is resistant to adsorption of phosphopeptides.

The inventors have determined that chromatographic separation components employing a nickel-cobalt alloy that is limited in an amount of titanium to less than 1 wt % on wetted surfaces exhibit superior performance with respect to resistance to adsorption of biological sample components (e.g., proteins and peptides) as compared to stainless steel components when performing chromatographic separation of biological samples. Further, the inventors determined that decreasing the amount of titanium in the alloy improved the quality of the chromatographic separation. In particular, the inventors determined that a separation column with wetted surfaces of MP35N LT alloy did not show significant peak broadening or peak tailing during analysis of histidine-containing peptides. Further, the inventors determined that a separation column with wetted surfaces of MP35N LT did not require conditioning of the column and showed consistent peak width over successive injections during analysis of peptide-containing samples. The impressive performance of a nickel-cobalt alloy in chromatographic separation of samples with peptides and proteins was unexpected, as nickel ions and cobalt ions are known to chelate certain types of peptides or proteins by metal chelation interaction chromatography, which would lead to the expectation that nickel and cobalt in an alloy would lead to greater interaction with peptides or proteins. Experimental results comparing the performance of stainless steel, fused silica, and MP35N LT alloy chromatographic separation components during separation of samples with biological components are detailed below in the examples section with respect to FIGS. 11 to 15.

Turning again to the device 10 of FIGS. 1A-1E, in some embodiments, most or all of the thickness of the wall 12 may be made of the alloy. For example, FIG. 1D shows a detail view of the wall 12, in which the most or all of the thickness of the wall 12 is made of the alloy material (e.g., MP35N LT), in accordance with some embodiments.

Figure 1E:
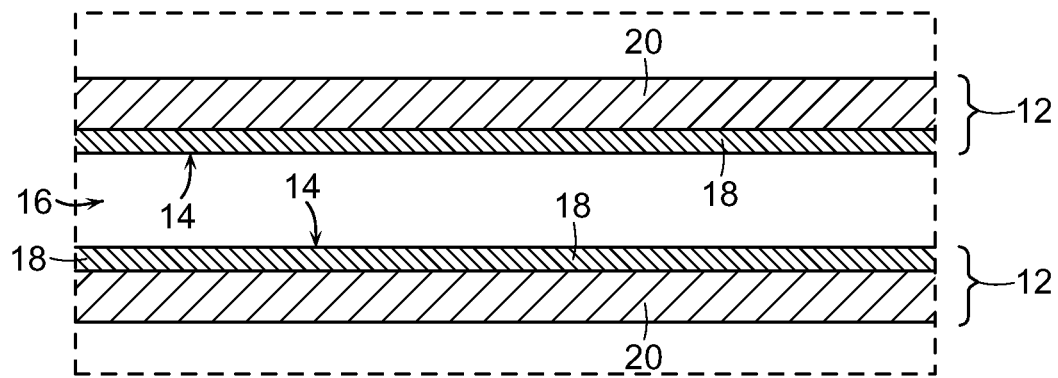
FIG. 1E is a detail view of FIG. 1B showing a portion of a wall having a surface portion and a bulk portion, in accordance with some embodiments.

In some embodiments, the wall 12 includes a surface portion including the wetted surface and a bulk portion, and the composition of the alloy material of the wetted surface is different than a composition of a material of the bulk portion. For example, FIG. 1E shows a detail view, in accordance with another embodiment, in which the wall 12 includes a surface portion 18 and a bulk portion 20. The wetted surface 14 is disposed on the surface portion 18 of the alloy material (e.g., MP35N LT) and the bulk portion 20 has a different composition (e.g., stainless steel). The material of the bulk portion 20 may be selected for desirable mechanical properties or chemical properties (e.g., strength or corrosion resistance) and/or for issues relating to cost (e.g., the material of the bulk portion may be less expensive than the alloy material). Other materials that could be employed for the bulk portion include, but are not limited to stainless steel, titanium, aluminum, carbon fiber composites, PEEK, polyolefins, ceramics, etc. In some embodiments, the surface portion 18 is deposited on the bulk portion 20. In some embodiments, the surface portion 18 is diffusion bonded to the bulk portion 20. In some embodiments, the surface portion 18 is welded to the bulk portion 20. In some embodiments, the bulk portion 20 is a sleeve around and in contact with the surface portion 18.

In some embodiments the wetted surface 14 consists of the alloy material. In some embodiments, most of the surface area of the wetted surface is covered by the alloy material. In some embodiments, over 90% of the surface area of the wetted surface is covered by the alloy material. In some embodiments, over 95% of the surface area of the wetted surface is covered by the alloy material. In some embodiments, over 98% of the surface area of the wetted surface is covered by the alloy material. In some embodiments, over 99% of the surface area of the wetted surface is covered by the alloy material.

In some embodiments, the wetted surface 14 of the wall 12 defines a separation channel 16, as shown. In some embodiments, the alloy is employed in the wall 12 of the separation channel 16 or in at least a surface portion 18 of the wall 12 of the separation channel 16. In some embodiments, the alloy is also employed in one or more wetted surfaces of one or more additional components of the device 12.

Figure 1F:
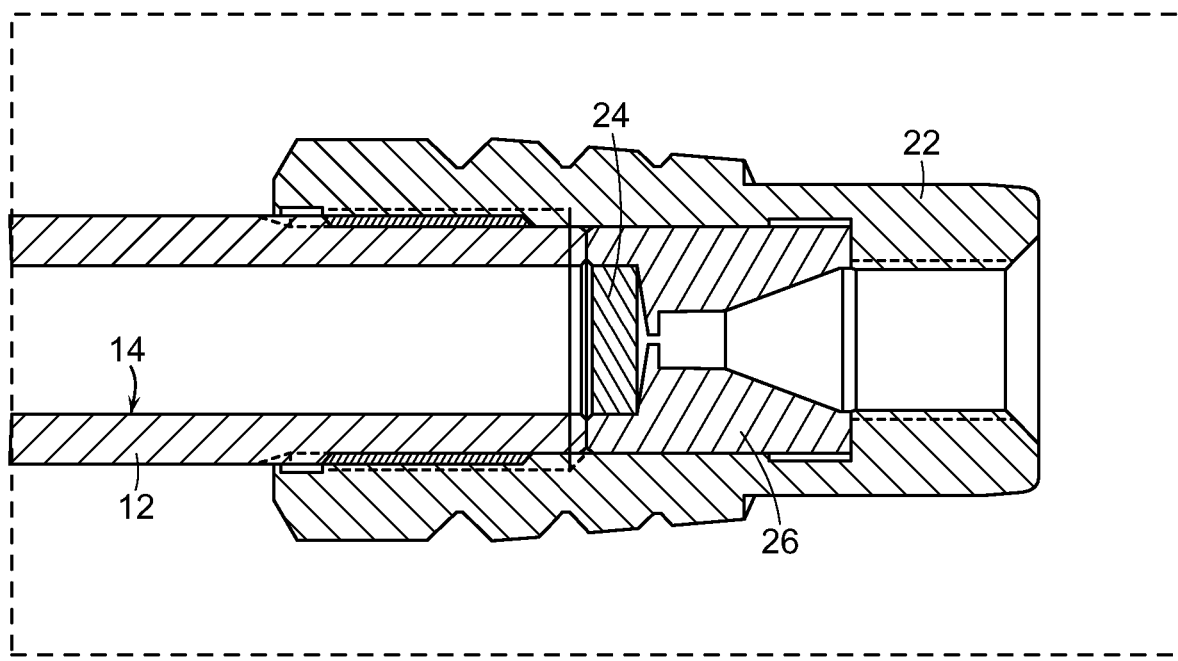
FIG. 1F is a detail view of FIG. 1B showing an end of the column assembly.
Figure 2A:
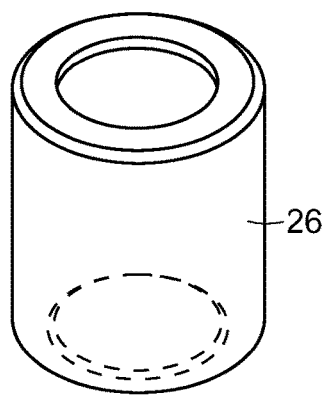
FIG. 2A is a perspective view of a housing, in accordance with an embodiment.
Figure 2B:
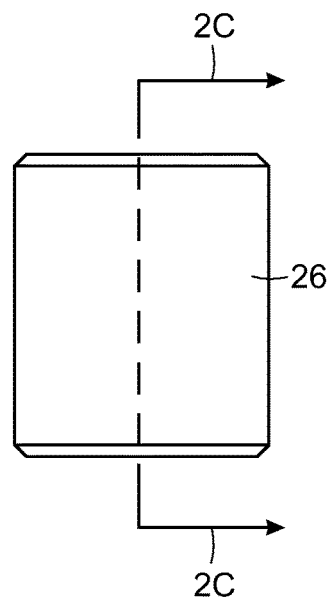
FIG. 2B is a side view of the housing of FIG. 2A.
Figure 2C:
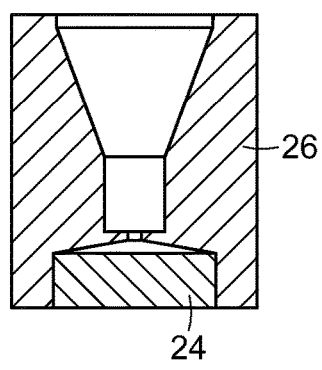
FIG. 2C is a side cross-sectional view of the housing of FIG. 2B.
Figure 2D:
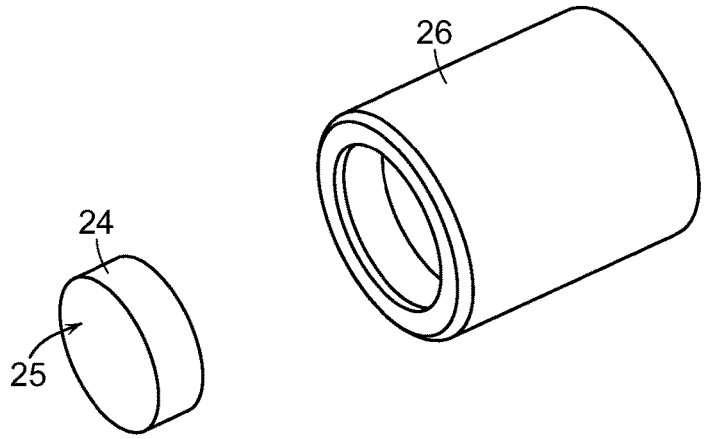
FIG. 2D is an exploded perspective view of the housing of FIG. 2A and an associated frit.

For example, in some embodiments, the device 10 also includes an end fitting 22 and wetted surfaces of the end fitting comprise the alloy material (see detail view of FIG. 1F). In some embodiments the device 10 also includes a frit 24 and wetted surfaces 25 of the frit 24 comprise the alloy material (see FIG. 1F). In some embodiments, the device 10 further includes a housing 26 that includes the frit 24. The detail view of FIG. 1F shows the housing 26 and the frit 24 as part of the column assembly device 10. FIGS. 2A-2D show different views of the housing 26.

Figure 3:
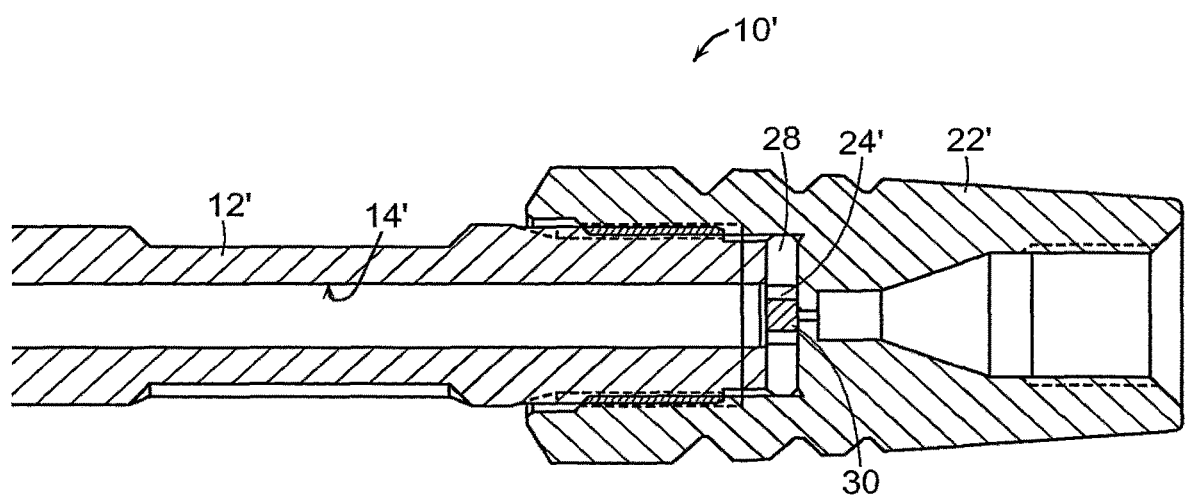
FIG. 3 is a cross-sectional view of an end of a column assembly including a seal ring in accordance with an embodiment.
Figure 4A:
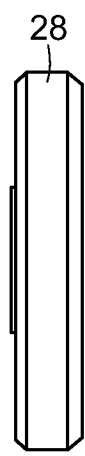
FIG. 4A is a side view of a seal ring in accordance with an embodiment.
Figure 4B:
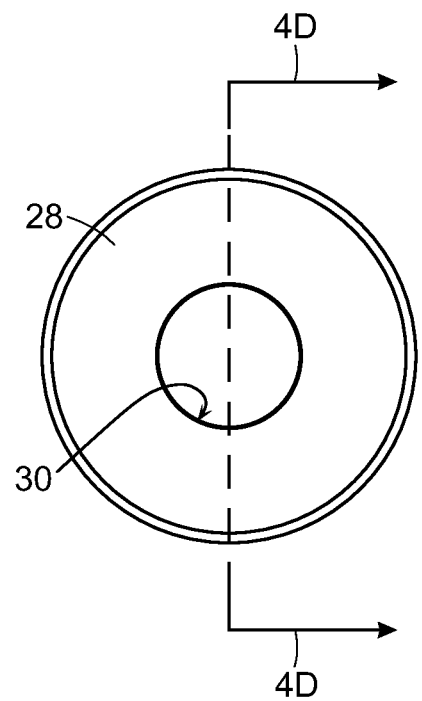
FIG. 4B is a front view of the seal ring of FIG. 4A.
Figure 4C:
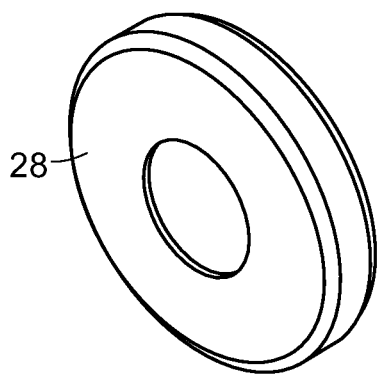
FIG. 4C is a perspective view of the seal ring of FIG. 4A.
Figure 4D:
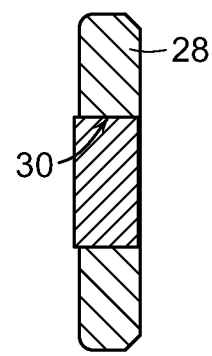
FIG. 4D is a side cross-sectional view of the seal ring of FIG. 4A.

In some embodiments, a device also includes a seal ring 28 and a wetted surface 30 of the seal ring includes the alloy material. FIG. 3 depicts a cross-sectional view of an end of a column assembly 10' that includes a wall 12', a wetted surface 14', an end fitting 22', a frit 24' and a seal ring 28 with wetted surface 30. FIGS. 4A-4D depict different views of the seal ring 28.

In some embodiments, the device 10 also includes a distributor disk 32 and wetted surfaces 33 of the distributor disk 32 comprise the alloy (see FIGS. 5A and 5B). FIG. 5C shows the distributor disk 32 and a housing assembly 35 with an associated filter or frit 34. In some embodiments, a housing assembly 35 including the distributor disk 32 and associated filter or frit 34 is located upstream and downstream of the wall of the separation column.

The chromatographic separation assembly would normally include a stationary phase (not shown) within the separation channel 16. In some embodiments of the device, all surfaces of the device 10 upstream of and outlet end of the separation channel 16 and configured to be in contact with the mobile phase including the sample during use, excluding the stationary phase, comprise the alloy material. For example in some embodiments, wetted surfaces of the wall 12, the end fittings 22 and the frit 24 include the alloy material.

Embodiments include components for use in a device for separating a sample by chromatography. The component has a body having a wetted surface exposed to a mobile phase including the sample during chromatographic separation, The wetted surface includes an alloy material as described above with respect to the device embodiments. For example, in some embodiments the component is the wall 12 having a wetted surface 14 that defines a chromatographic separation channel 16. In some embodiments, the component is an end fitting 22. In some embodiments, the component is a frit 24 and the wetted surface is a wetted surface of the frit 24. In some embodiments, the component is a stationary phase retaining element configured to keep a stationary phase within a separation channel of the device. In some embodiments, the stationary phase retaining element is a frit 24. In some embodiments, the frit additionally or alternatively filters solid particulates upstream of a chromatographic separation channel. In some embodiments, the frit is upstream of a chromatographic separation channel and may be used to keep particulates off of a separate column inlet frit directly upstream of the chromatographic separation channel.

Figure 6A:
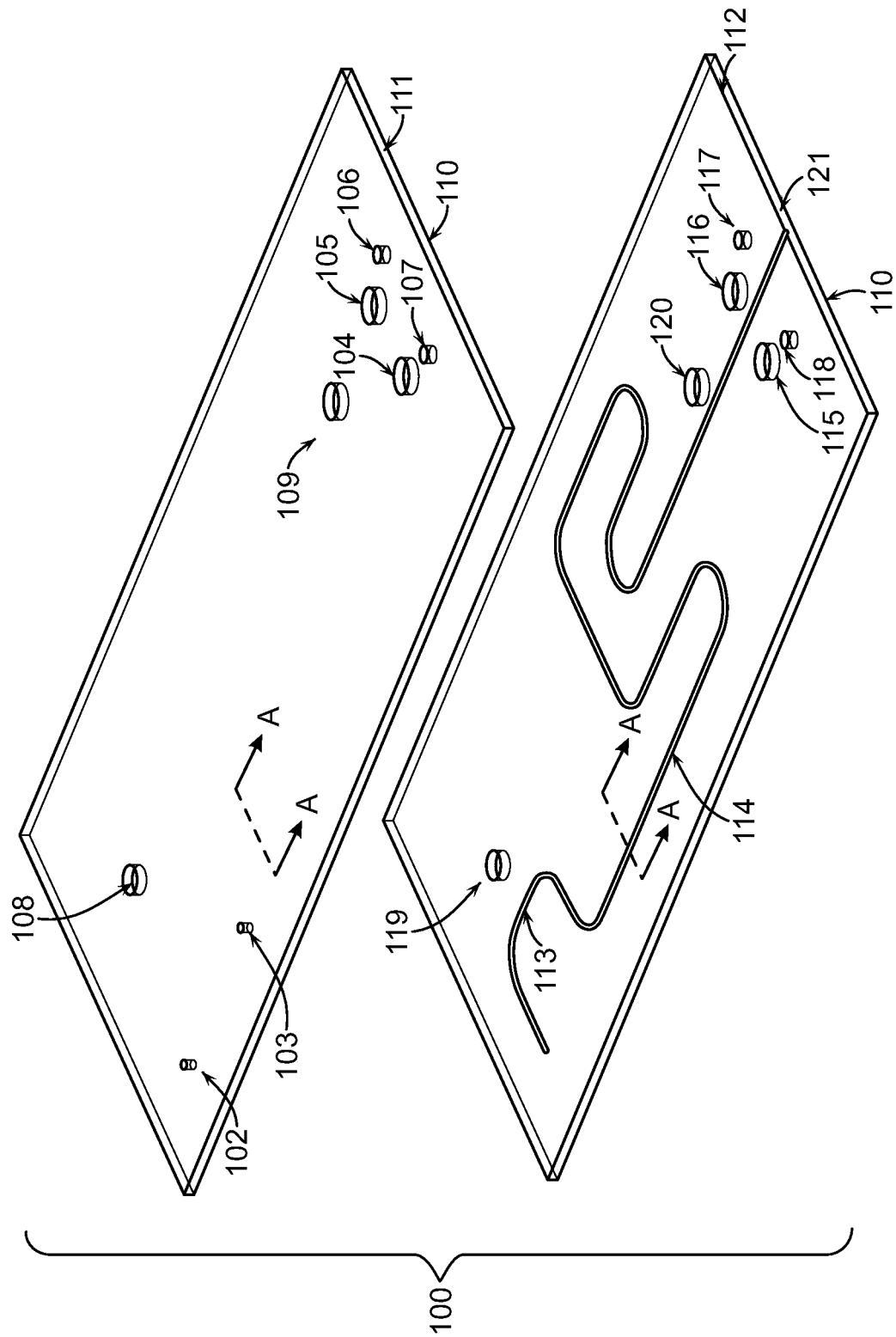
FIG. 6A is an exploded perspective view of a two layer planar chromatographic device in accordance with an embodiment.

Embodiments are not limited to chromatographic separation devices with cylindrical columns. One of ordinary skill in the art will appreciate that embodiments of chromatographic separation devices may employ other geometries for separation channels. For example, device 100 shown in FIGS. 6A through 9B has a planar chromatographic chip geometry. Device 100 may alternately be described as a component configured for use in a device for separating a sample by chromatography. FIG. 6A is an exploded view of the layers of the device 100. The device 100 includes a first layer 111 (e.g., a top plate) and a second layer 112 (e.g., a bottom plate). The second layer 112 includes grooves 113 and 114, which may be formed by electrochemical micromachining (EMM), also known as electroetching or electrochemical micromachining through a photomask, or milling, that form portions of a chromatographic separation channel. The first layer 111 includes holes 102, 103, 104, 105, 106, 107, and 108 and slot 109, and the second layer 10b includes holes 115, 116, 117, 118 and 119 and slot 120, which may be made by micro electrical discharge machining (micro-EDM), wire EDM, mechanical drilling, and/or laser drilling. Holes 102 and 103 are used as fluidic access ports or vias. Holes 104, 105, 106, 107, 115, 116, 117 and 118 are used to attach a fitting at an exterior edge of the device 100 to provide fluidic access on the edge or side 110 of the device 100. Holes 108, 119 and slots 109, 120 are used for alignment of the first layer 111 and the second layer 112.

The first layer 111 is joined to the second layer 112 to form device 100. In some embodiments, the first layer 111 is joined to the second layer 112 by diffusion bonding or other suitable techniques, such as clamping with a gasket seal. FIG. 6B schematically depicts a cross-sectional view of the device taken through line A-A of FIG. 6A after the first layer 111 and the second layer 112 have been joined together. FIGS. 6A and 6B are not to scale and some relative dimensions are changed for ease of illustration. As shown in FIG. 6B, after the joining of the first layer 111 and the second layer 112, the groove 114 and a surface of the first layer 111 form a channel 122 capable of holding fluids hermetically under high hydraulic pressures. Similarly, groove 113 and the first layer 111 form another portion of channel 122 when the first layer 111 and the second layer 112 are joined. In some embodiments, a width w of the channel 122 is in a range of 50-500 µm.

The first layer 111 and the second layer 112 together form a wall of the device with wetted surface 124. Alternatively, the first layer 111, the second layer 202 may be described as together forming a body having a wetted surface 124. The wetted surface 124 includes the alloy that includes the following constituents: nickel; and cobalt and/or chromium; and limited in an amount of titanium to 1 wt %. All of the features and variations of the alloy described above with respect to device 10 are also applicable to device 100.

In some embodiments, the first layer 111 and the second layer 112 each include a surface portion and a bulk portion as depicted in FIG. 6C. The first layer 111 includes a surface portion 126 including the alloy and a bulk portion 128 of a different material (e.g., stainless steel) and the second layer 112 includes a surface portion 130 including the alloy and a bulk portion 132 of a different material (e.g., stainless steel). The bulk portion and the surface portion may be joined together by any suitable techniques, which include, but are not limited to, diffusion bonding, clamping, overmolding, etc.

Figure 7B:
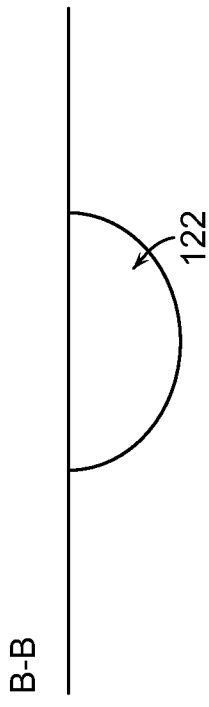
FIG. 7B is a cross-sectional view of the weir of FIG. 7A taken along line B-B.
Figure 7C:
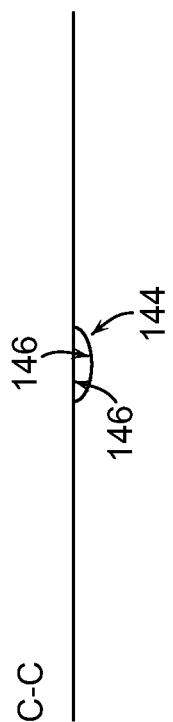
FIG. 7C is a cross-sectional view of the weir of FIG. 7A taken along line C-C.
Figure 7A:
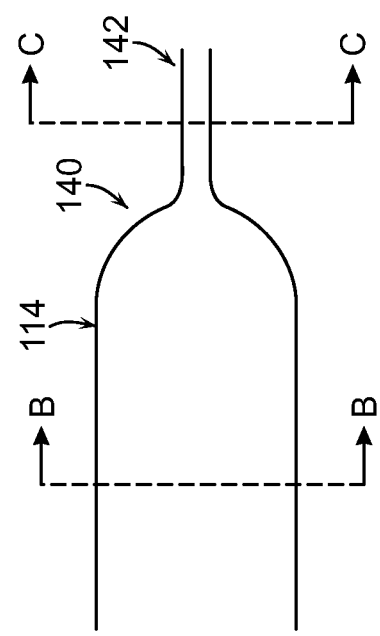
FIG. 7A is a top view of a weir, in accordance with some embodiments.
Figure 8A:
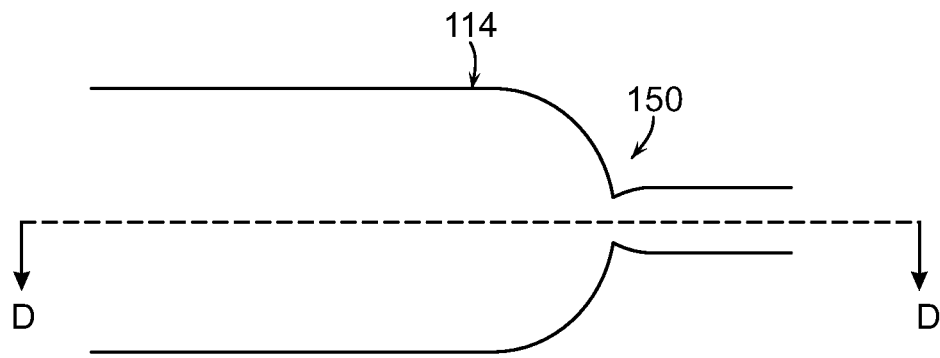
FIG. 8A is a top view of a weir having a neck between a wider channel and a narrower channel in accordance with some embodiments.
Figure 8B:
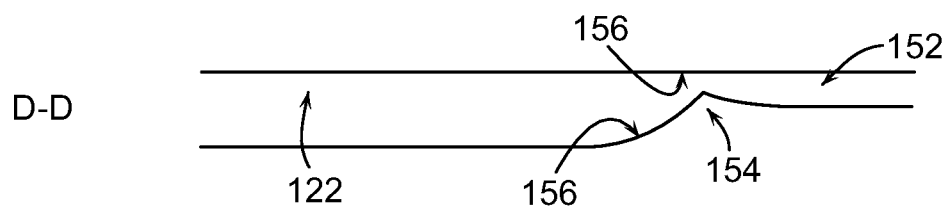
FIG. 8B is a cross-sectional view of the weir of FIG. 8A taken along line D-D.

After fabrication and bonding or joining of the first layer and the second layer, the channel 122 is normally packed with a stationary phase (e.g., micrometer sized particles). The device 100 may include one or more stationary phase retaining elements at the end or ends of a separation column portion of the channel 122 to prevent the stationary phase from flowing out of the channel 122. In some embodiments, the stationary phase retaining element is a frit, which may be formed by sintering the stationary phase particles together in some portion of the separation column or by immobilizing some of the stationary phase particles using some other suitable method. In some embodiments, the stationary phase retaining element is a weir formed in the device 100 by narrowing a portion of the groove 114 formed in the second layer 112 thereby narrowing the corresponding portion of the resulting channel. For example, FIG. 7A-7C schematically depict a weir included in device 100, in accordance with some embodiments. Groove 114 narrows at weir 140 forming a narrowed groove 142 and corresponding narrowed channel 144 downstream of the weir. The weir 140 has a wetted surface 146. As another example, FIGS. 8A-8B schematically depict an alternative geometry of a weir included in device 100, in accordance with some embodiments. In FIGS. 8A-8B, groove 114 narrows and becomes shallower at weir 150 and then widens and deepens to form two channels 122, 152 respectively, connected by a narrower and shallower neck 154. The weir 150 has a wetted surface 156. In some embodiments, a plurality of weirs may be formed at the end of a channel. In some embodiments, a wetted surface or wetted surfaces of one or more stationary phase retaining elements include the alloy. For example, a wetted surface 146 of weir 140 or a wetted surface of weir 150 includes the alloy in some embodiments.

Figure 9B:
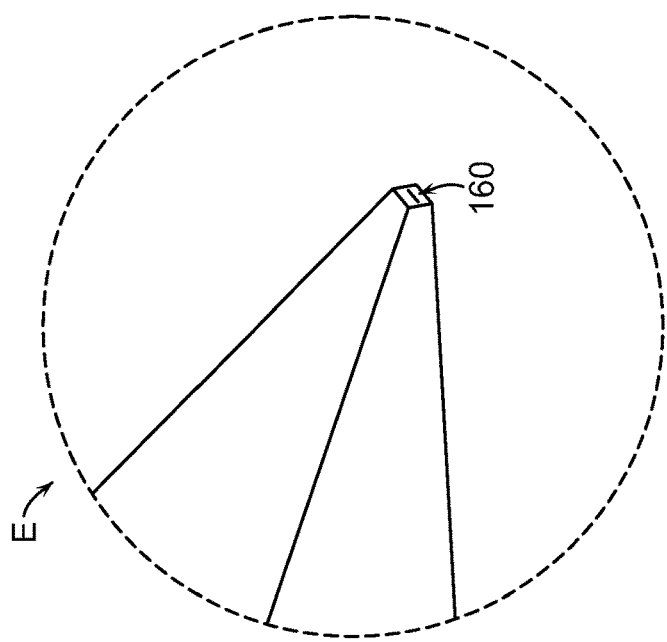
FIG. 9B is a detail view of the electrospray tip of FIG. 9A.
Figure 9A:
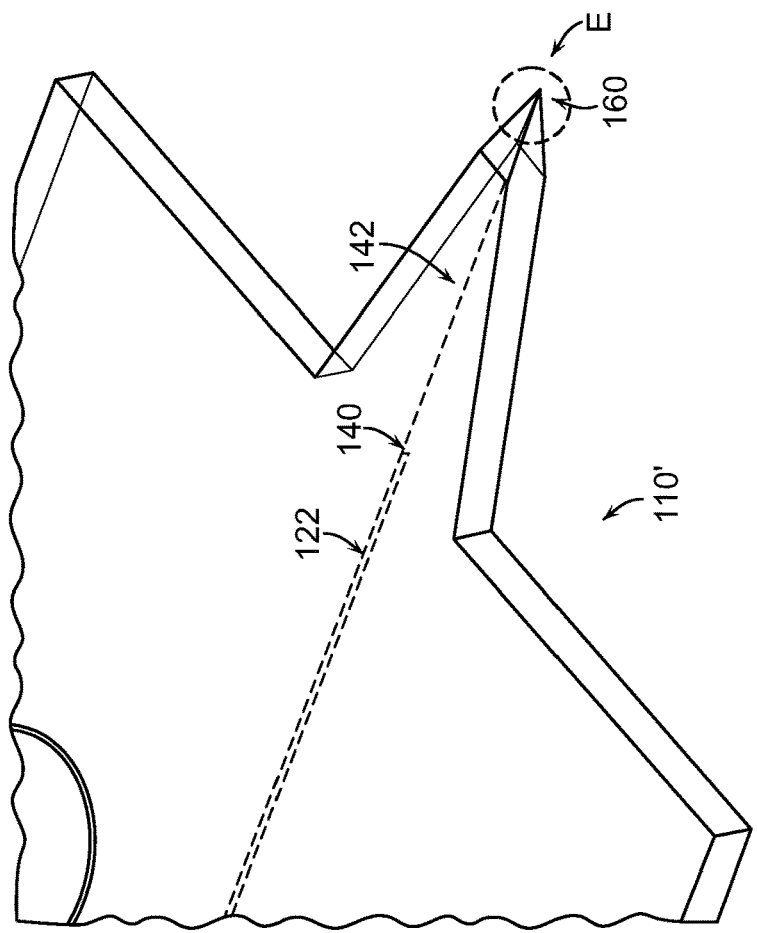
FIG. 9A is a perspective view of an end portion of a device having an electrospray tip, in accordance with some embodiments.

In some embodiments, the device 100 includes an electrospray tip. For example, FIGS. 9A and 9D show an embodiment of an end 110' of the device having an integrated electrospray tip 160. The electrospray tip 160 is formed by cutting the end 110 of the device 100 (e.g., using EMM and/or EDM) to form the tip geometry. Channel 122 narrows at weir 140 to become narrowed channel 142, which exits the device 100 at the electrospray tip 160. In some embodiments, a wetted surface of the electrospray tip includes the alloy.

In some embodiments, the device 100 further includes one or more integrated valves (not shown), and wetted surfaces of the one or more integrated valves include the alloy material.

In some embodiments, a device may include three layers employing slots to define a channel. For example, FIGS. 10A-10C schematically depict a device 200 having a first layer 201, second layer 202, and a third layer 203. Device 200 may alternately be described as a component configured for use in a device for separating a sample by chromatography. The first layer 201 has similar holes and slots as those described above with respect to first layer 111 of device 100. The second layer 202 has similar holes and slots as those described above with respect to second layer 111 of device 100; however, instead of grooves, the second layer 202 has slots 213 and 214. The third layer 203 has holes and slots for alignment similar to those described above with respect to second layer 111 of device 100. First layer 201, second layer 202 and third layer 203 are joined together. The cross-sectional view in FIG. 10B depicts how surfaces of the first layer 201 and the third layer 203 and the slot 214 of the second layer 202 form a hermetically sealed channel 222. When joined together, the first layer 201, the second layer 202 and the third layer 203 can be described as forming a wall of the device 200. Alternatively, the first layer 201, the second layer 202 and the third layer 203 can be described as forming a body of the device 200. Surfaces of the slot 214 and surfaces of the first layer 201 and third layer 203 form the wetted surfaces 224 of the wall or body, which include the alloy.

In some embodiments, the first layer 201 and the third layer 203 each include a surface portion and a bulk portion as depicted in FIG. 10C. The first layer 201 includes a surface portion 226 including the alloy and a bulk portion 228 of a different material (e.g., stainless steel) and the third layer 203 includes a surface portion 230 including the alloy and a bulk portion 232 of a different material (e.g., stainless steel). The bulk portion and the surface portion may be joined together by any suitable techniques, which include, but are not limited to, diffusion bonding, clamping, overmolding, etc.

Additional information regarding planar geometry chromatographic separation devices and manufacturing methods for such devices appears in U.S. Patent Publication No. 2013/0014567 entitled "Chromatography Apparatus Having Diffusion-Bonded And Surface-Modified Components," which is incorporated by reference herein in its entirety. In some embodiments, the separation device may be part of a microfluidic cartridge.

In some embodiments, the device is configured for low pressure applications. For example, the device could be configured for use in solid phase extraction. In another embodiment, the device is configured for use in supercritical fluid chromatography (SFC). In another embodiment, the device is configured for use in gas chromatography. Low pressure applications, as used herein, refers to applications in which the pressure in the device falls within a range of atmospheric pressure to 1000 psi.

In some embodiments, the device is configured to withstand pressures used in high performance liquid chromatography. As used herein, high performance liquid chromatography refers to liquid chromatography in which the mobile phase is subjected to pressures of between 1,000 and 6,000 psi.

In some embodiments, the device is configured to withstand pressures used in ultra-high performance liquid chromatography. As used herein, ultra high performance liquid chromatography refers to liquid chromatography in which the mobile phase is subjected to pressures of greater than 6,000 psi.

In some embodiments, the device is configured to withstand pressures of 6,000 to 15,000 psi during use. In some embodiments, the device is configured to withstand pressures of 6,000 psi to 18,000 psi during use. In some embodiments, the device is configured to withstand pressures of 15,000 to 20,000 psi during use. In some embodiments, the device is configured to withstand pressures of 20,000 psi to 50,000 psi during use.

In some embodiments, a width or diameter of a separation channel of a device or component falls in a range of 10 μm to 25 mm. In some embodiments, a width or diameter of a separation channel of a device or component falls in a range of 20 μm to 7.8 mm. For a prep column, a width or diameter may be as large as 100 mm. In some embodiments, such as a microfluidic device or a microfluidic component, a width or diameter of a separation column may be in the range of 20 μm to 500 μm.

The use of the alloy for a wetted surface of a device or component may be particularly beneficial in a microfluidic system, as opposed to using surface-treated stainless steel for wetted surfaces because of the difficulties associated with accomplishing effective surface treatment in microfluidic systems.

The use of the alloy for a wetted surface of a device or component may be beneficial, as compared to using surface treated fused silica because it is easier to manufacture separation columns from metals such as the alloy than from silica, and because the silanols of the fused silica wetted surface can interact with proteins and peptides by ion exchange.

Solely for illustrative purposes, use of devices taught herein will be described with reference to device 10 described above with respect to FIGS. 1A-1F In use, a chromatographic separation device 10 including a separation channel 16 is provided. The separation channel 16 has wetted surfaces 14 including an alloy material. The alloy material includes the following constituents nickel; and cobalt and/or chromium; and limited in an amount of titanium to 1 wt %. Other features and aspects of the alloy material in accordance with various embodiments are described above. A mobile phase is flowed carrying the sample into and through the separation channel 16, thereby performing chromatographic separation on the sample. In some embodiments, the method further includes detecting components of the sample. In some embodiments, the sample includes proteins and the proteins in the sample are separated and detected. In some embodiments, the sample includes peptides and the peptides in the sample are separated and detected. In some embodiments, the sample includes histidine-containing peptides and the histidine-containing peptides in the sample are separated and detected. In some embodiments, the sample includes phosphopeptides and the phosphopeptides in the sample are separated and detected. In some embodiments, the sample includes one or more of peptides or proteins and the one or more proteins or peptides in the sample are separated and detected with a U.S. Pharmacopeia (USP) tailing factor of less than 1.3. The USP tailing factor is calculated as the ratio of the width of a peak to 2 times the width of the front of the peak both measured at 5% of the height of the peak as indicated in the formula for tailing factor below:

$$T = \frac{f_{5\%} + t_{5\%}}{2 f_{5\%}}$$

where T is the tailing factor $f_{5\%}$ is the width of the front of the peak at 5% of maximum peak height and $t_{5\%}$ is the width of the tail of the peak at 5% of maximum peak height.

Another aspect provides a variety of separation devices having a stationary phase including an alloy material described herein. In various embodiments, separation devices with a stationary phase including an alloy material described herein include, for example, chromatographic columns; thin layer plates; filtration membranes; sample cleanup devices and microtiter plates; packings for HPLC columns; solid phase extraction (SPE) devices; ion-exchange chromatography devices; magnetic beads; affinity chromatographic and SPE sorbents; sequestering reagents; solid supports for combinatorial chemistry; solid supports for oligosaccharide, polypeptides, and/or oligonucleotide synthesis; solid supported biological assays; capillary biological assay devices for mass spectrometry; templates for controlled large pore polymer films; capillary chromatography devices; electrokinetic pump packing materials; packing materials for microfluidic devices; polymer additives; catalysis supports; and packings materials for microchip separation devices.

In some embodiments, alloy materials as described herein can be packed into preparatory, microbore, capillary, and microfluidic devices. In some embodiments, a solid stationary phase in a device includes the alloy materials as described herein. In some embodiments, surfaces of a solid stationary phase in a device include the alloy materials described herein. In some embodiments, both the solid phase and a wetted surface of a wall of the device include an alloy or alloys as described herein.

Embodiments can be used for all modes of chromatography. Separation modes include but are not limited to reversed phase, normal phase, size exclusion, ion exchange, affinity, hydrophobic interaction and hydrophilic interaction. In addition, the alloys described herein can be employed in sample preparation devices for all the above modes.

Some embodiments include an immobilized enzymatic reactor (IMER). In some embodiments, the IMER includes a wall defining a chamber having an inlet and an outlet and a solid stationary phase covalently linked to an enzyme within the chamber. In use, a liquid sample including a polymer and an analyte flows into the chamber through the inlet, interacts with the immobilized enzyme and flows out of the chamber through the outlet. In some embodiments, the solid stationary phase of the IMER includes an alloy described herein. In some embodiments a wetted surface of the wall of the chamber (i.e., a surface that is in contact with the liquid sample during use) includes an alloy described herein. In some embodiments, both a wetted surface of the wall of the chamber and the solid stationary phase of the IMER include one or more of the alloys described herein. In some embodiments, the IMER device includes additional components or fittings and wetted surfaces of one or more of the additional components or fittings include one or more alloys described herein. In some embodiments, the IMERs are suitable for operation under pressures in the range of about 2,500 to 35,000 psi. In some embodiments, the IMERs are suitable for operation under pressures in the range of 8,000 to 15,000 psi. Additional details regarding IMER devices and systems are provided in U.S. Patent Application Publication No. 2014/0162298, published Jun. 12, 2014 and entitled "Immobilized Enzymatic Reactor," which is incorporated herein by reference in its entirety. In some embodiments, the chamber of the IMER may have a configuration similar to that of chromatographic separation devices described herein. One of ordinary skill in the art in view of the present disclosure will appreciate that the drawings and description herein regarding devices, columns and components for chromatographic separation also applies, in large part to IMERs. For example, a structure described herein as a separation column or a separation channel may also or alternatively be viewed and described as a chamber in which a stationary phase can be disposed for an IMER.

Enzymes that could be immobilized on the stationary phase in an IMER include, but are not limited to: pepsin, protease, cellulose, lipase, amylase, glucoamylase, glucose isomerase, xylanase, phtase, arabinanase, polygalacturonase, hydrolase, chymosin, urease, pectinase, beta-gluc333nase, ligase, glycosidase, polymerase, phosphatase, kinase, ceramidase. In certain embodiments, the enzyme is trypsin, PNGase F, pepsin, chymotrypsin, peptidase, bromelain, papain, IdeS, or IdeZ, or mixtures thereof.

In some embodiments, the stationary phase includes immobilized affinity reagents, which include, but are not limited to: Protein G, Lambda, Kappa, Protein Y, Protein L, aptamers, affimers, amyloids, lectins, or activated resins for user generated affinity phases such as streptavidin and epoxy. The target molecules of the immobilized affinity reagents include, but are not limited to: proteins, IgG, IgM, insulin, peptides, small molecules, toxins, afflatoxins, mycotoxins, citrinin, deoxynivalenol, vomitoxin, fumonisin, ochratoxin, zearalenone, fusarium, or mixtures thereof. In some embodiments, the immobilized affinity immobilized affinity reagents or the target molecules of immobilized affinity reagents are incorporated into a technology platform such as the Stable Isotope Standards and Capture by Anti-Peptide Antibodies (SISCAPA) affinity workflow from SISCAPA Assay Technologies Inc. (see e.g., U.S. Pat. Nos. 9,274,124; 9,261,506; 9,170,263; 9,163,276; 9,018,580; 8,916,680; 8,633,031; 8,580,491; 8,574,860; 8,569,071; 8,568,988; 8,455,202; 8,187,893; 8,119,356; 8,097,425; 7,955,810; and 7,807,172).

In some embodiments, the stationary phase is modified to include one or more immobilized affinity and immobilized enzyme materials.

In some embodiments, a column for a separation device or for an IMER has an inner diameter of 1.0 mm, 2.1 mm, 3.0 mm, 4.6 mm, 10 mm, 19 mm, 30 mm ID, or a diameter there between. In some embodiments, a column for a separation device or for an IMER has an inner diameter falling in a range of 0.5-100 mm.

In some embodiments, a column for a separation device or for an IMER has a length of 5 mm, 10 mm, 30 mm, 50 mm, 75 mm, 100 mm, 150 mm, 200 mm, 300 mm 500 mm, 1000 mm, 2000 mm length, or a length falling there between.

In some embodiments, a component for a separation device or for an IMER is compatible with or configured to be used with 1 mm ID column hardware, 2.1 mm ID column hardware, 3.0 mm ID column hardware, 4.6 mm I D column hardware, 10 mm ID column hardware, 19 mm ID column hardware, 30 mm ID column hardware, 0.5-100 mm ID column hardware, planar geometry chromatographic separation devices, diffusion-bonded separation devices, or microfluidic cartridges, In some embodiments, incorporating the alloy materials described herein into devices may improve the lifetimes of the devices due to the improved corrosion resistance of the alloy material as compared with other materials normally used on surfaces of such devices. Embodiments of devices that have a stationary phase including an alloy as described herein may exhibit improved lifetimes. Embodiments of devices that have one or more wetted surfaces that include an alloy as described herein may exhibit improved lifetimes.

Experimental data showing the improved corrosion resistance of chromatographic hardware made of the alloys disclosed herein as compared with the corrosion resistance of stainless steel is presented below in the examples section.

Some embodiments provide a kit including a device or one or more components of a device as described herein, and instructions for use. In one embodiment, the instructions are for use with a separation device, e.g., chromatographic columns, thin layer plates, filtration membranes, sample cleanup devices, solid phase extraction device, microfluidic device, and microtiter plates. In one embodiment, the instructions are for use with an immobilized enzymatic reactor device.

EXAMPLES

Comparison of Chromatographic Separation of Samples Including Peptides Using Nickel-Cobalt Alloy, Stainless Steel, and Silica Columns The inventors performed chromatographic separation on samples including peptides to compare the performance of conventional stainless steel and silica separation columns to example separation columns.

Figure 11:
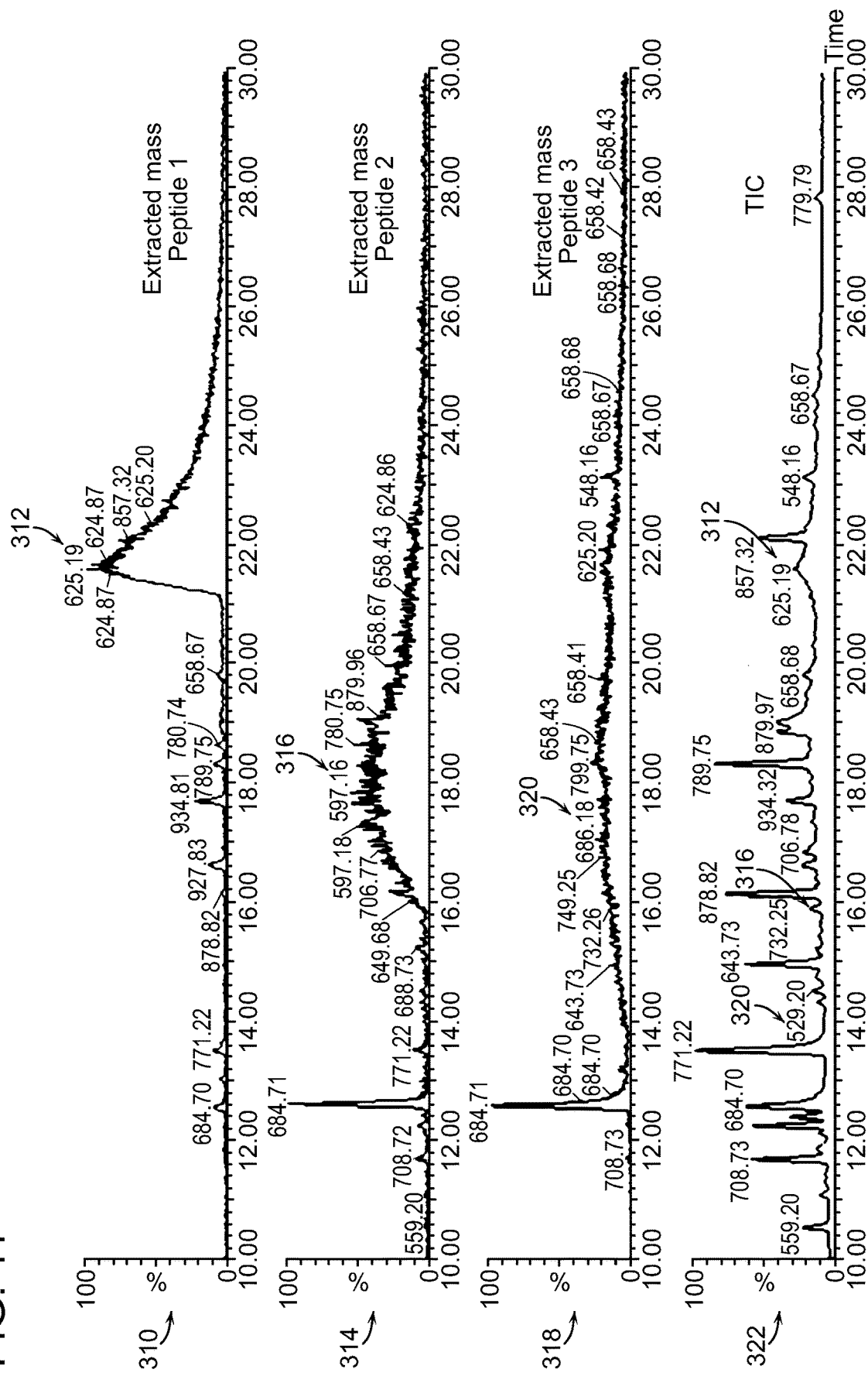
FIG. 11 includes chromatograms of a tryptic digest of a sample of enolase performed using a stainless steel column.

FIG. 11 includes chromatograms of a tryptic digest of a sample of enolase analyzed with a conventional stainless steel separation column. Chromatogram 310 shows significant peak broadening for an extracted mass 312 of peptide 1 in the sample. Chromatogram 314 shows significant peak broadening for an extracted mass 316 of peptide 2 in the sample. Chromatogram 318 shows even more significant peak broadening for an extracted mass 320 of peptide 3 in the sample. Chromatogram 322 of the total ion current shows the broadened peaks 312, 316, 320 for peptide 1, peptide 2 and peptide 3 respectively. The peaks for peptides 1, 2 and 3 show relatively low signal to noise ratio in addition to significant broadening. These chromatograms illustrate a problem with the use of a stainless steel column for samples including peptides. When a sample including enolase is analyzed on the stainless steel column, some peptides such as histidine-containing peptides do not appear in the chromatogram or have extremely broad peak shape, often observed with significant peak tailing. The peptides are tryptic digests of enolase, which are included in the MASSPREP Enolase Digest with Phosphopeptides Mix available from Waters Corporation of Milford, Mass. Peptide 1 is T3 (sequence WLTGPQLADLYHSLMK), Peptide 2 is T44 (sequence AAQDSFAAGWGVMVSHR) and Peptide 3 is T51-52 (sequence IEEELGDNAVF-AGENFHHGDKL). Further information regarding the peptides are available in the publication "MASSPREP ENOLASE DIGEST WITH PHOSPHOPEPTIDES MIX—Care and Use Manual" by Waters Corporation, which is available at http://www.waters.com/webassets/cms/support/docs/715001713.pdf, the contents of which is incorporated herein in its entirety.

Figure 12:
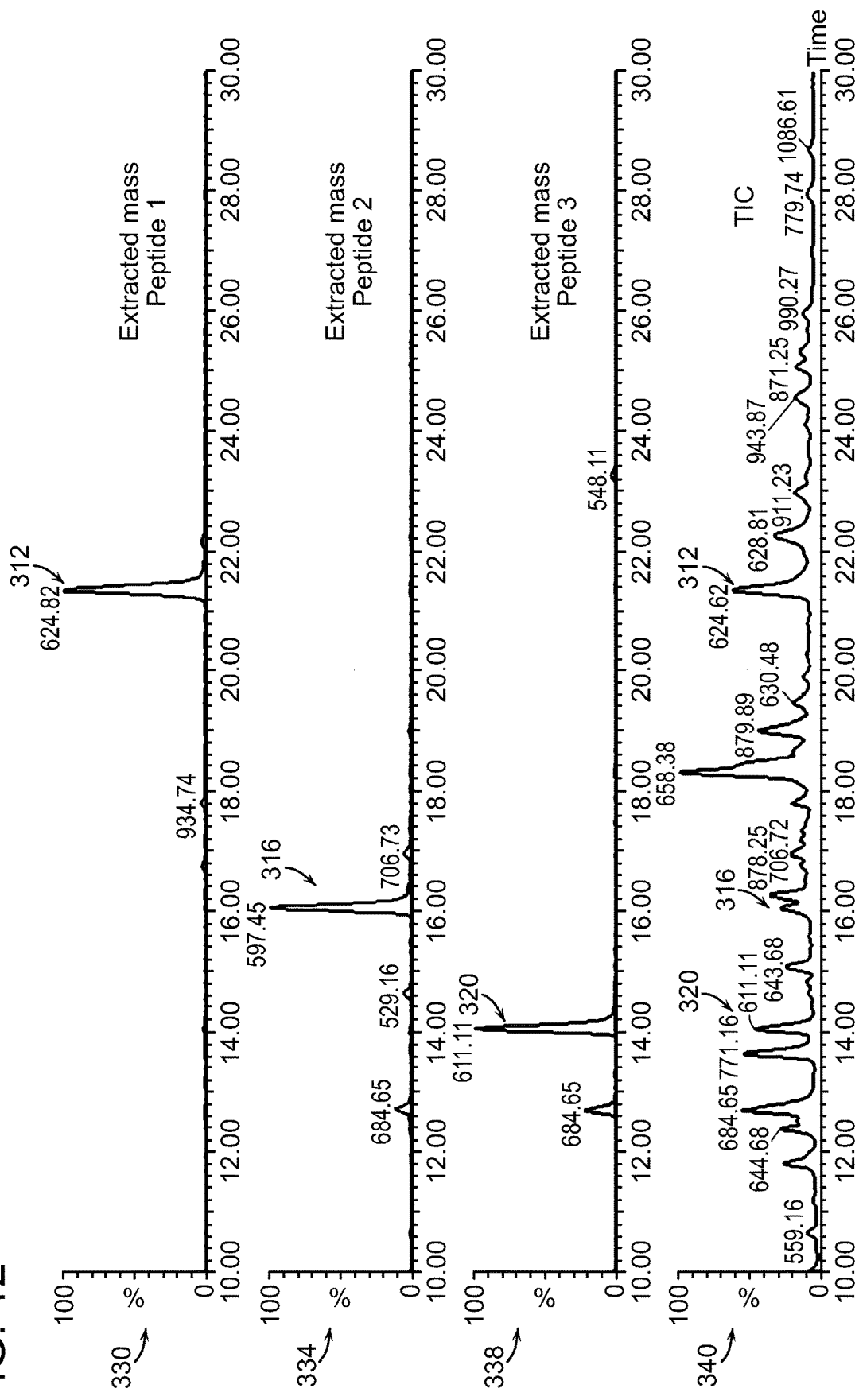
FIG. 12 includes chromatograms of a tryptic digest of a sample of enolase performed using a fused silica column.
Figure 15:
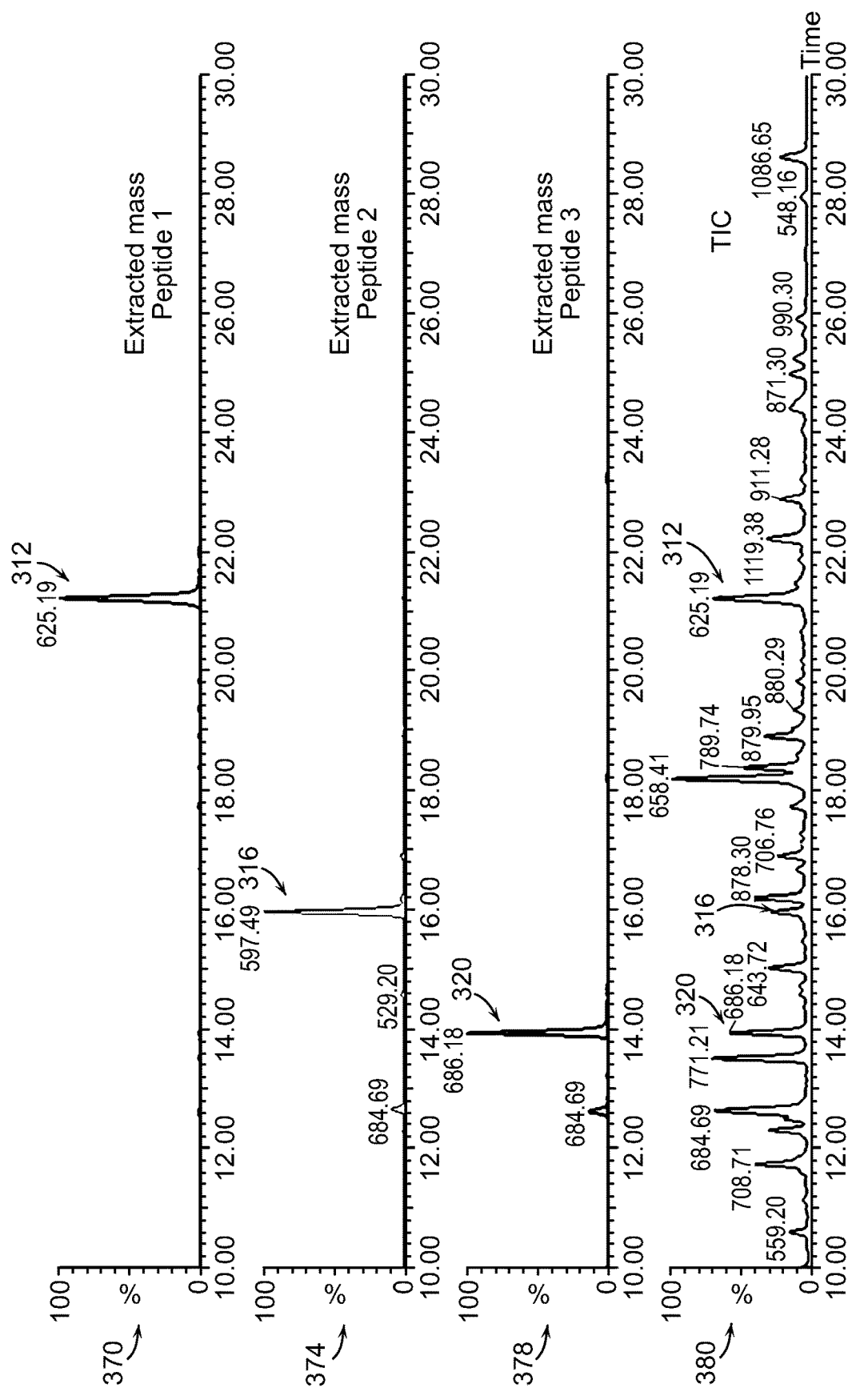
FIG. 15 includes chromatograms of a sample of an enolase tryptic digest performed using an example column, in accordance with some embodiments.

For comparison, FIG. 12 includes chromatograms of a tryptic digest of the same sample of enolase analyzed with a column constructed with fused silica tubing, specifically the NANOEASE column from Waters Corporation of Milford, Mass. In contrast to chromatogram 310 from the stainless steel column, chromatogram 330 shows a narrow peak and high signal to noise ratio for the extracted mass 312 of peptide 1 in the sample. In contrast to chromatogram 314 from the stainless steel column, chromatogram 334 shows a narrow peak and high signal to noise ratio for the extracted mass 316 of peptide 2 in the sample. In contrast to chromatogram 318 from the stainless steel column, chromatogram 338 shows a narrow peak and high signal to noise ratio for the extracted mass 320 of peptide 3 in the sample. Chromatogram 340 shows the total ion current and the excellent signal to noise ratio of peaks 312, 316, 320 for peptide 1, peptide 2 and peptide 3 respectively. The contrast between the chromatograms in FIG. 11 and FIG. 12 illustrates how poor the stainless steel column performed for separation of these three peptides.

Another problem with the stainless steel column hardware is that for some peptides, it takes several injections to obtain acceptable peak shape, indicating that the column needs to be conditioned for the analysis. Graph 350 in FIG. 13 shows how the peak width of a peptide significantly changes over 10 injections in a stainless steel column, demonstrating that the stainless steel column requires substantial conditioning to obtain consistent results. Such conditioning wastes sample and experimental time. In contrast, graph 360 of FIG. 14 demonstrates how the peak width for the peptide is consistent from injections 2 through 10 indicating that the fused silica column does not need significant conditioning.

Although the fused silica column performed well for these three peptides, fused silica may be an undesirable material for many applications due to the difficulty in making devices and components from fused silica as compared with making devices and components from a metal material.

Some surface modifications can be made in a stainless steel separation column for better performance with peptide containing samples such as surface passivation of wetted surfaces or coatings that can be applied to wetted surfaces (e.g., creating an iron-deficient and chromium-rich surface or coating with polymers); however, such surface modifications and coatings can fail if the surface or coating is damaged during use. Further, such surface treatments and coatings are difficult to accomplish in microscale devices. Embodiments employing the alloys described herein avoid the need for surface treatments or coatings on wetted surfaces thereby reducing complexity in manufacturing.

An example separation column was constructed using a nickel-cobalt alloy material, specifically, MP35N LT, for the column hardware. This alloy has approximately 35 wt % cobalt, 35 wt % nickel, 20 wt % chromium, and 10 wt % molybdenum with less than 0.01 wt % titanium. The example separation column was used for separation and detection of the enolase peptide sample, with the results shown in FIGS. 15 and 16.

In contrast to chromatogram 310 for the stainless steel column, chromatogram 370 for the example column shows a narrow peak and high signal to noise ratio for the extracted mass 312 of peptide 1 in the sample. In contrast to chromatogram 314 for the stainless steel column, chromatogram 374 for the example column shows a narrow peak and high signal to noise ratio for the extracted mass 316 of peptide 2 in the sample. In contrast to chromatogram 318 for the stainless steel column, chromatogram 378 for the example column shows a narrow peak and high signal to noise ratio for the extracted mass 320 of peptide 3 in the sample. Chromatogram 380 for the example column shows the total ion current and the excellent signal to noise ratio for peaks 312, 316, 320 for peptide 1, peptide 2 and peptide 3, respectively. The contrast between the graphs in FIGS. 11 and 15 demonstrates the superior performance of the example column as compared to the stainless steel column for separation and detection of these three peptides. Peptides whose peaks were broadened or missing in the stainless steel column data are present, narrow, and have good signal to noise ratio in the example column data. Comparison of FIG. 15 for the example column and FIG. 12 for the fused silica column shows that the example column performed at least as well as fused silica for separation and detection of the three peptides.

Figure 16:
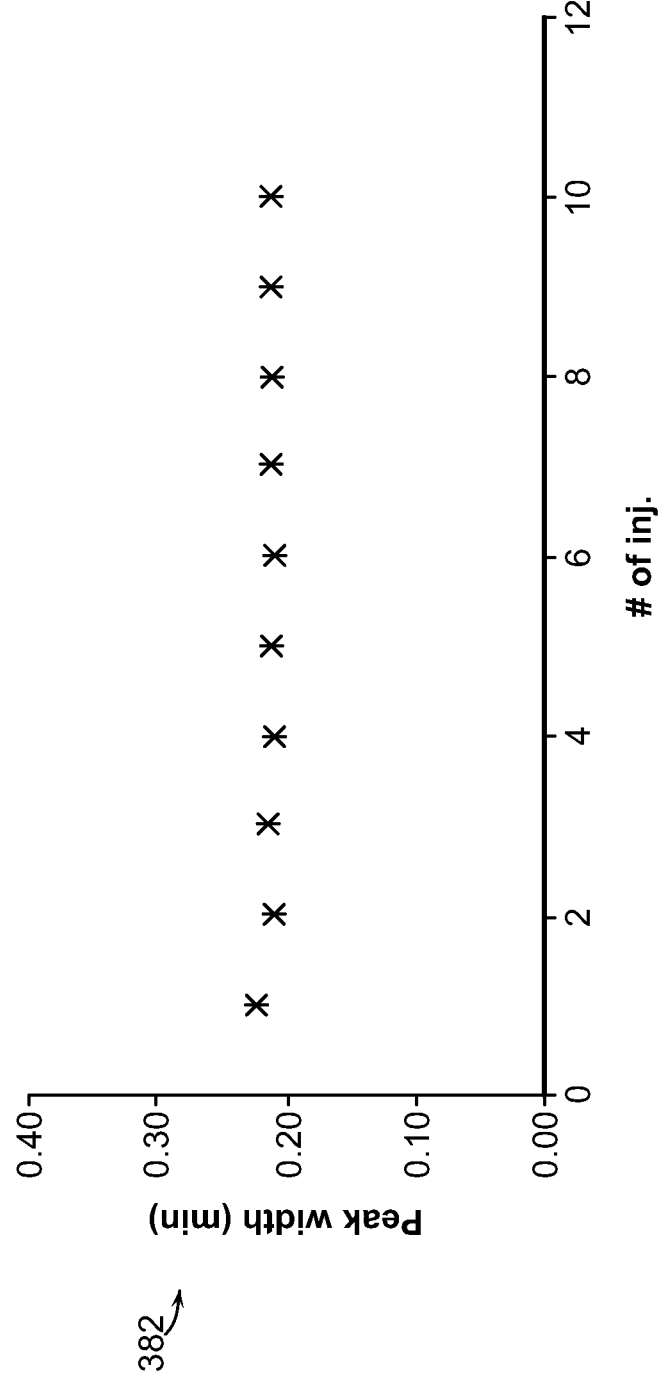
FIG. 16 is a plot of peak width as a function of injection number during analysis of a sample of an enolase tryptic digest performed using the example column.

FIG. 16 includes a graph 382 of peptide peak width for subsequent sample injections in the example column. As shown, there was very little peak width variation for the second to tenth sample injections demonstrating that the example column did not need conditioning, unlike the stainless steel column. Thus, use of the example column would save sample and time by avoiding the need for column conditioning, relative to use of the stainless steel column.

As noted above, nickel ions and cobalt ions are known to chelate certain types of peptides or proteins by metal chelation interaction chromatography, which would indicate that a nickel-cobalt alloy may not be desirable for reducing interactions with peptides and proteins. However, the inventors have demonstrated the unexpected result that a nickel-cobalt alloy with less than 1 wt % titanium showed less interaction with the peptides as compared stainless steel.

The alloys described herein are also expected to perform well in applications such as ion-exchange separations, size exclusion chromatography (SEC), and other applications where high buffer and salt concentrations are commonly used. To counteract the poor performance of stainless steel, columns for these classes of separations commonly employ materials such as glass and PEEK, both of which can limit the design pressure of the columns and/or significantly affect the cost and complexity of the column design.

Figure 17:
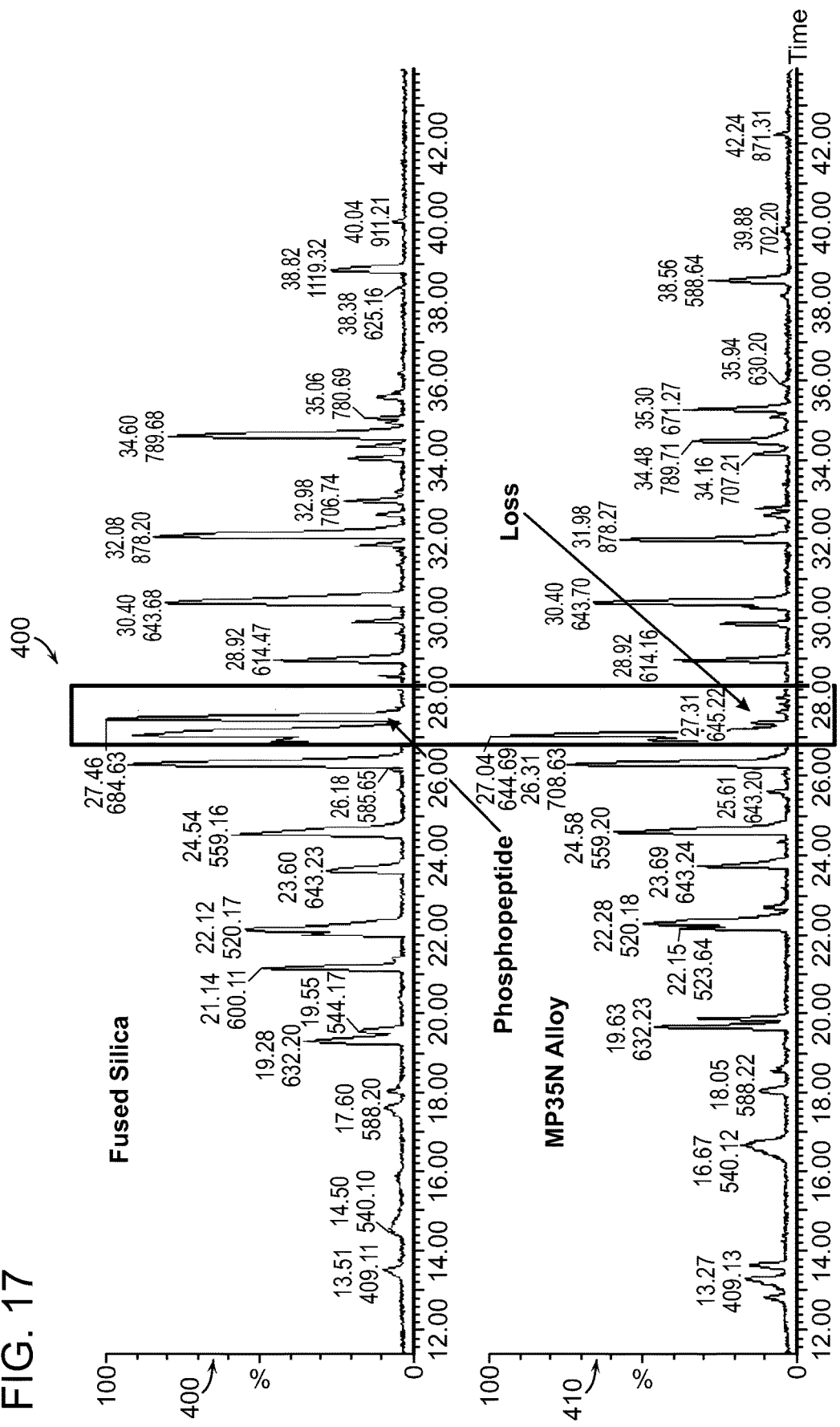
FIG. 17 includes chromatograms of analysis of a sample of an enolase tryptic digest performed using fused silica tubing and performed using tubing of a nickel-cobalt alloy having 1 wt % titanium.

In the process of developing the invention, the inventors also explored nickel-cobalt alloys having higher levels of titanium. For these experiments described below, a sample of tubing material was placed in line with a separation column and was exposed to the pressure gradient and to the sample during sample separation. The reference tubing material was fused silica and the tubing material being evaluated was MP35N, a trademarked alloy of SPS Technologies, LLC of Jenkintown, Pa., which includes 35 wt % cobalt, 35 wt % nickel, 20 wt % chromium, 10 wt % molybdenum, and about 1 wt % titanium FIG. 17 includes LC/MS chromatograms for a sample including enolase peptides for both the fused silica tubing (chromatogram 400) and for the MP35N tubing (chromatogram 410). As shown, a phosphopeptide that was clearly present in the chromatogram 400 produced with the system including the fused silica tube was absent from the chromatogram 410 produced with the system including the MP35N tube as indicated by box 412. Thus, the inventors determined that the adsorption of peptides is sensitive to titanium levels in the alloy and that titanium levels in the nickel-cobalt alloy should be less than 1 wt % titanium.

IMER Using Nickel-Cobalt Alloy Column

An immobilized enzymatic reactor is prepared by packing a stationary phase of porous particles having immobilized pepsin on the surface of the particles in UPLC column hardware (2.1×30 mm) made from MP35N. The packed MP35N column was used with an ultra performance liquid chromatography system, specifically, the NANOACQUITY ULTRAPERFORMANCE LC system from Waters Corp. of Milford, Mass. Further details regarding preparing and using an IMER with a column made from a different material appear in U.S. Patent Application Publication No. 2014/0162298, published Jun. 12, 2014 and entitled "Immobilized Enzymatic Reactor," which is incorporated herein by reference in its entirety. The packed MP35N column withstands elevated pressures, exhibits good digestive performance, and exhibits decreased adsorptive losses of peptides that are generated in the on-line digestion as compared with traditional stainless steel hardware.

Improved Corrosion Resistance of Nickel-Cobalt Alloy Column

Having low or minimal corrosion, rusting, or metals leaching from the chromatographic hardware is very important in several types of separations, including (but not limited to): ion-exchange chromatography, ion-chromatography, Size Exclusion Chromatography, Reversed-Phase Chromatographic, Hydrophobic Interaction Chromatography, Hydrophilic interaction chromatography, Gel Permeation chromatography, Normal-Phase Chromatography, Chiral Chromatography, Supercritical Fluid Chromatography, and Subcritical Fluid Chromatography. The avoidance of corrosion in chromatographic hardware is especially important in ion-exchange chromatography. To avoid corrosion when exposed to mobile phases that are high or low pH, and contain elevated salt, many commercial suppliers of ion-exchange columns use non-metallic hardware, such as plastic columns and in particular PEEK chromatographic hardware.

It should be noted that plastic or PEEK chromatographic hardware is not suitable for ultra performance liquid chromatography. It is difficult to efficiently pack chromatographic media under the required pressures for ultra performance liquid chromatography when the chromatographic hardware includes PEEK or is plastic lined steel, and the use conditions for ultra performance liquid chromatography are above the normal operating range for plastic or PEEK chromatographic hardware.

As such there is a need for mechanically strong, pressure tolerant chromatographic hardware with a lower propensity toward corrosion than stainless steel, that can be used for ultra performance liquid chromatography.

To compare corrosion resistance, stainless steel and nickel-cobalt alloy material (specifically, MP35N LT) chromatographic column hardware tubes (2.1×100 mm) were separately filled with an acid (20 mM 1,4-dimethylpiperazine buffer with 1M NaCl and 0.05% sodium azide, adjusted to pH 3.5 using dilute hydrochloric acid), capped at either end with plastic fittings, and stored at 60° C. for one week. As explained above, MP35N LT is a low titanium grade (less than 0.01 wt % Ti) of MP35N. Following this acid exposure, the tubes were emptied into plastic vials. The two samples along with a control acid solution were analyzed for metals content (ICP-MS, VHG Labs, Manchester N.H., uncertainty estimated at +/−10%). The results of these studies are shown in the table below.

| Levels of Metals in Acid Stored in Tubes of Various Materials | | | |
| --- | --- | --- | --- |
| | Acid control sample | Acid Stored in Stainless Steel Column | Acid Stored in MP35N LT Column |
| Iron (ppb) | <100 | 3861 | 359 |
| Cobalt (ppb) | | <20 | 1559 |
| Chromium (ppb) | <20 | 672 | 325 |
| Nickel (ppb) | <10 | 460 | 1001 |
| Molybdenum (ppb) | <10 | <10 | <10 |
| Manganese (ppb) | <10 | 92 | <10 |
| Total Metals (ppb) | | 5115 | 3264 |

Increased levels of metals present in the acid solution stored in the tubes of stainless steel and MP35N LT as compared with the control acid solution evidences a reaction between acid and the metal surface indicating corrosion occurred. As shown in the table, the acid stored in the MP35N LT column had a reduced overall metal concentration as compared to the acid stored in the stainless steel column. As such, one can conclude that the MP35N LT had reduced corrosion with acid exposure when compared with traditional stainless steel chromatographic columns. This corrosion resistance indicates that low titanium nickel-cobalt alloys, such as MP35N LT, which are mechanically strong enough to be used for ultra performance liquid chromatography, may be particularly useful for a variety of chromatographic separations, including (but not limited to): ion-exchange chromatography, ion-chromatography, Size Exclusion Chromatography, Reversed-Phase Chromatographic, Hydrophobic Interaction Chromatography, Hydrophilic interaction chromatography, Gel Permeation chromatography, Normal-Phase Chromatography, Chiral Chromatography, Supercritical Fluid Chromatography, and Subcritical Fluid Chromatography. The use of MP35N LT chromatographic hardware is especially suited for the use in ion-exchange chromatography, and ultra performance ion-exchange liquid chromatography.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A device for separating a sample by chromatography, the device comprising:
   a body for containing a mobile phase, the body defined by a wall having a wetted surface exposed to the mobile phase including the sample during chromatographic separation, the wetted surface of the wall including an alloy material comprising the following constituents:
   nickel; and
   cobalt and/or chromium; and
   limited in an amount of titanium to 1 wt %.

2. The device of claim 1, wherein the alloy material is limited in an amount of titanium to 0.1 wt %.

3. The device of claim 1, wherein the alloy material is limited in an amount of titanium to 0.05 wt %.

4. The device of claim 1, wherein the alloy material further comprises molybdenum as a constituent.

5. The device of claim 1, wherein the alloy material comprises the following constituents:
   25 wt %-45 wt % cobalt;
   25 wt %-45 wt % nickel;
   10 wt %-30 wt % chromium; and
   0 wt %-20 wt % molybdenum; and
   a remainder being limited to a total of 5 wt %.

6. The device of claim 5, the remainder being limited to a total of 3 wt %.

7. The device of claim 1, wherein the wall comprises a surface portion including the wetted surface and a bulk portion, and wherein the composition of the alloy material of the wetted surface is different than a composition of a material of the bulk portion.

8. The device of claim 7, wherein the surface portion is diffusion bonded to the bulk portion.

9. The device of claim 7, wherein the surface portion consists of the alloy material.

10. The device of claim 1, wherein the device is configured to withstand pressures of 6,000 psi to 15,000 psi during use.

11. The device of claim 1, wherein the device is configured to withstand pressures of 15,000 to 20,000 psi.

12. The device of claim 1, wherein the wetted surface of the wall defines a separation channel.

13. The device of claim 12, further comprising an end fitting, wherein exterior surfaces of the end fitting exposed to the mobile phase comprise the alloy material.

14. The device of claim 12, further comprising a frit, wherein exterior surfaces of the frit exposed to the mobile phase comprise the alloy material.

15. The device of claim 12, further comprising a weir, wherein exterior surfaces of the weir exposed to the mobile phase comprise the alloy material.

16. The device of claim 12, wherein the device is a microfluidic device and the width or diameter of the separation channel falls in a range of 20 μm to 500 μm.

17. The device of claim 12, wherein the device comprises two or more sheets of the alloy material, a portion of each sheet forming a portion of the wall, the two or more sheets being diffusion bonded at an interface with at least a portion of the separation channel extending along the interface.

18. The device of claim 12, wherein the device comprises two or more sheets, each sheet including a layer of the alloy material, each sheet forming a portion of the wall with the layer of alloy material of the sheet forming the wetted surface for the portion of the wall, the layers of the alloy material of the two or more sheets being diffusion bonded at an interface with at least a portion of the separation channel extending along the interface.

19. The device of claim 1, wherein the alloy material is resistant to adsorption of histidine-containing peptides.

20. The device of claim 1, wherein over 95% of the surface area of the wetted surface consists of the alloy material.

\* \* \* \* \*